(12) United States Patent
Tokhtuev et al.

(10) Patent No.: US 9,001,319 B2
(45) Date of Patent: Apr. 7, 2015

(54) SELF-CLEANING OPTICAL SENSOR

(75) Inventors: Eugene Tokhtuev, Duluth, MN (US); Christopher J. Owen, Duluth, MN (US); Anatoly Skirda, Hermantown, MN (US); William M. Christensen, Hibbing, MN (US)

(73) Assignee: Ecolab USA Inc., Saint Paul, MN (US)

( * ) Notice: Subject to any disclaimer, the term of this patent is extended or adjusted under 35 U.S.C. 154(b) by 168 days.

(21) Appl. No.: 13/464,508

(22) Filed: May 4, 2012

(65) Prior Publication Data

US 2013/0293881 A1 Nov. 7, 2013

(51) Int. Cl.
*G01N 21/05* (2006.01)
*G01N 21/15* (2006.01)

(52) U.S. Cl.
CPC ............... *G01N 21/15* (2013.01); *G01N 21/05* (2013.01)

(58) Field of Classification Search
CPC ............... A47L 5/14; A61L 2/10; A61L 2/28; G01N 21/15; G01N 21/05; G01N 21/85; B08B 3/02; B08B 5/02
USPC ........... 356/244, 246, 432–440; 15/50.1, 320; 359/507; 250/574, 576, 438, 239
See application file for complete search history.

(56) References Cited

U.S. PATENT DOCUMENTS

| | | | |
|---|---|---|---|
| 3,426,794 A | 2/1969 | Freytag | |
| 3,609,048 A | 9/1971 | Strickler | |
| 3,628,028 A * | 12/1971 | Thorsheim | 250/576 |
| 3,734,601 A | 5/1973 | Heiss | |
| 3,861,198 A * | 1/1975 | Shea | 73/61.41 |
| 3,895,406 A * | 7/1975 | Fannon, Jr. | 15/302 |
| 3,901,656 A | 8/1975 | Durkos et al. | |
| 3,917,404 A | 11/1975 | Heiss | |
| 3,954,341 A | 5/1976 | Uffenheimer | |
| 4,008,397 A | 2/1977 | Zdrodowski | |
| 4,108,602 A | 8/1978 | Hanson et al. | |
| 4,108,972 A | 8/1978 | Dreyer | |
| 4,114,038 A | 9/1978 | Parker | |
| 4,180,739 A | 12/1979 | Abu-Shumays | |
| 4,271,123 A | 6/1981 | Curry et al. | |
| 4,275,300 A | 6/1981 | Abbott | |
| 4,279,509 A | 7/1981 | Daffern | |
| 4,377,880 A | 3/1983 | Jackson et al. | |
| 4,440,497 A | 4/1984 | Carey et al. | |
| 4,527,114 A | 7/1985 | Coulter | |
| 4,575,424 A | 3/1986 | Allington et al. | |
| 4,738,528 A | 4/1988 | Craft | |
| 4,750,837 A | 6/1988 | Gifford et al. | |
| 4,802,768 A | 2/1989 | Gifford et al. | |
| 4,861,163 A | 8/1989 | Bach | |
| 4,867,559 A | 9/1989 | Bach | |
| 4,874,243 A | 10/1989 | Perren | |
| 4,896,047 A * | 1/1990 | Weaver et al. | 250/573 |
| 4,992,380 A | 2/1991 | Moriarty et al. | |
| 5,078,493 A | 1/1992 | Evens et al. | |

(Continued)

*Primary Examiner* — Hoa Pham
(74) *Attorney, Agent, or Firm* — Fredrikson & Byron, P.A.

(57) ABSTRACT

An optical sensor may include a sensor head that has an optical window for directing light into a flow of fluid and/or receiving optical energy from the fluid. The optical sensor may also include a flow chamber that includes a housing defining a cavity into which the sensor head can be inserted. In some examples, the flow chamber includes an inlet port defining a flow nozzle that is configured to direct fluid entering the flow chamber against the optical window of the sensor head. In operation, the force of the incoming fluid impacting the optical window may prevent fouling materials from accumulating on the optical window.

14 Claims, 9 Drawing Sheets

(56) References Cited

U.S. PATENT DOCUMENTS

| | | | |
|---|---|---|---|
| 5,140,169 | A | 8/1992 | Evens et al. |
| 5,185,531 | A * | 2/1993 | Wynn ............................ 250/431 |
| 5,250,186 | A | 10/1993 | Dollinger et al. |
| 5,269,937 | A | 12/1993 | Dollinger et al. |
| 5,414,508 | A | 5/1995 | Takahashi et al. |
| 5,422,719 | A | 6/1995 | Goldstein |
| 5,442,437 | A | 8/1995 | Davidson |
| 5,452,082 | A | 9/1995 | Sanger et al. |
| 5,471,294 | A | 11/1995 | Ogino |
| 5,485,277 | A | 1/1996 | Foster |
| 5,563,737 | A * | 10/1996 | Kamrat ........................ 359/509 |
| 5,736,405 | A | 4/1998 | Alfano et al. |
| 5,972,721 | A | 10/1999 | Bruno et al. |
| 6,300,638 | B1 | 10/2001 | Groger et al. |
| 6,303,316 | B1 | 10/2001 | Kiel et al. |
| 6,369,894 | B1 | 4/2002 | Rasimas et al. |
| 6,426,794 | B1 | 7/2002 | Trainoff |
| 6,452,672 | B1 | 9/2002 | Trainoff |
| 6,518,577 | B1 * | 2/2003 | Fang et al. .................... 250/372 |
| 6,627,873 | B2 * | 9/2003 | Tchakarov et al. ........... 250/256 |
| 6,635,224 | B1 | 10/2003 | Gui et al. |
| 6,670,614 | B1 | 12/2003 | Plut et al. |
| 6,670,617 | B2 | 12/2003 | Banks |
| 6,678,051 | B2 | 1/2004 | Gerner et al. |
| 6,755,079 | B1 | 6/2004 | Proett et al. |
| 6,780,306 | B2 | 8/2004 | Schlager et al. |
| 6,788,409 | B2 | 9/2004 | Goodwin |
| 6,992,488 | B2 | 1/2006 | Lin |
| 7,095,500 | B2 | 8/2006 | Banks |
| 7,099,012 | B1 | 8/2006 | Crawford et al. |
| 7,101,661 | B1 | 9/2006 | Heller et al. |
| 7,154,603 | B2 | 12/2006 | Banks |
| 7,209,223 | B1 | 4/2007 | Hull et al. |
| 7,231,833 | B2 | 6/2007 | McAllister et al. |
| 7,294,278 | B2 | 11/2007 | Spears et al. |
| 7,320,775 | B2 | 1/2008 | Kochy et al. |
| 7,431,883 | B2 | 10/2008 | Bell |
| 7,550,746 | B2 | 6/2009 | Tokhtuev et al. |
| 7,652,267 | B2 | 1/2010 | Tokhtuev et al. |
| 7,676,316 | B2 | 3/2010 | Lunati et al. |
| 7,858,035 | B2 * | 12/2010 | Cronin et al. ................. 422/68.1 |
| 7,867,718 | B2 | 1/2011 | Nilsson et al. |
| 7,909,963 | B2 | 3/2011 | Di Cesare |
| 7,920,260 | B2 | 4/2011 | Mantele et al. |
| 7,985,377 | B2 | 7/2011 | Vincent |
| 7,989,780 | B2 | 8/2011 | Tokhtuev et al. |
| 8,006,760 | B2 | 8/2011 | Fleming et al. |
| 8,614,793 | B2 * | 12/2013 | Tokhtuev et al. .............. 356/436 |
| 2003/0006385 | A1 | 1/2003 | Banks |
| 2003/0013849 | A1 | 1/2003 | Ward et al. |
| 2003/0183538 | A1 | 10/2003 | Lin |
| 2005/0069454 | A1 | 3/2005 | Bell |
| 2007/0141593 | A1 | 6/2007 | Lee et al. |
| 2008/0162016 | A1 | 7/2008 | Lunati et al. |
| 2009/0057145 | A1 | 3/2009 | Vincent |
| 2009/0255668 | A1 | 10/2009 | Fleming et al. |
| 2010/0007874 | A1 | 1/2010 | Lunati et al. |
| 2010/0042389 | A1 | 2/2010 | Farruggia et al. |
| 2010/0145630 | A1 | 6/2010 | Ball et al. |
| 2010/0168984 | A1 | 7/2010 | Fournel et al. |
| 2010/0209916 | A1 | 8/2010 | Zon |
| 2011/0240886 | A1 | 10/2011 | Tokhtuev et al. |
| 2011/0240887 | A1 | 10/2011 | Christensen et al. |
| 2011/0242539 | A1 | 10/2011 | Christensen et al. |
| 2013/0256557 | A1 * | 10/2013 | Tokhtuev et al. .............. 250/438 |

* cited by examiner

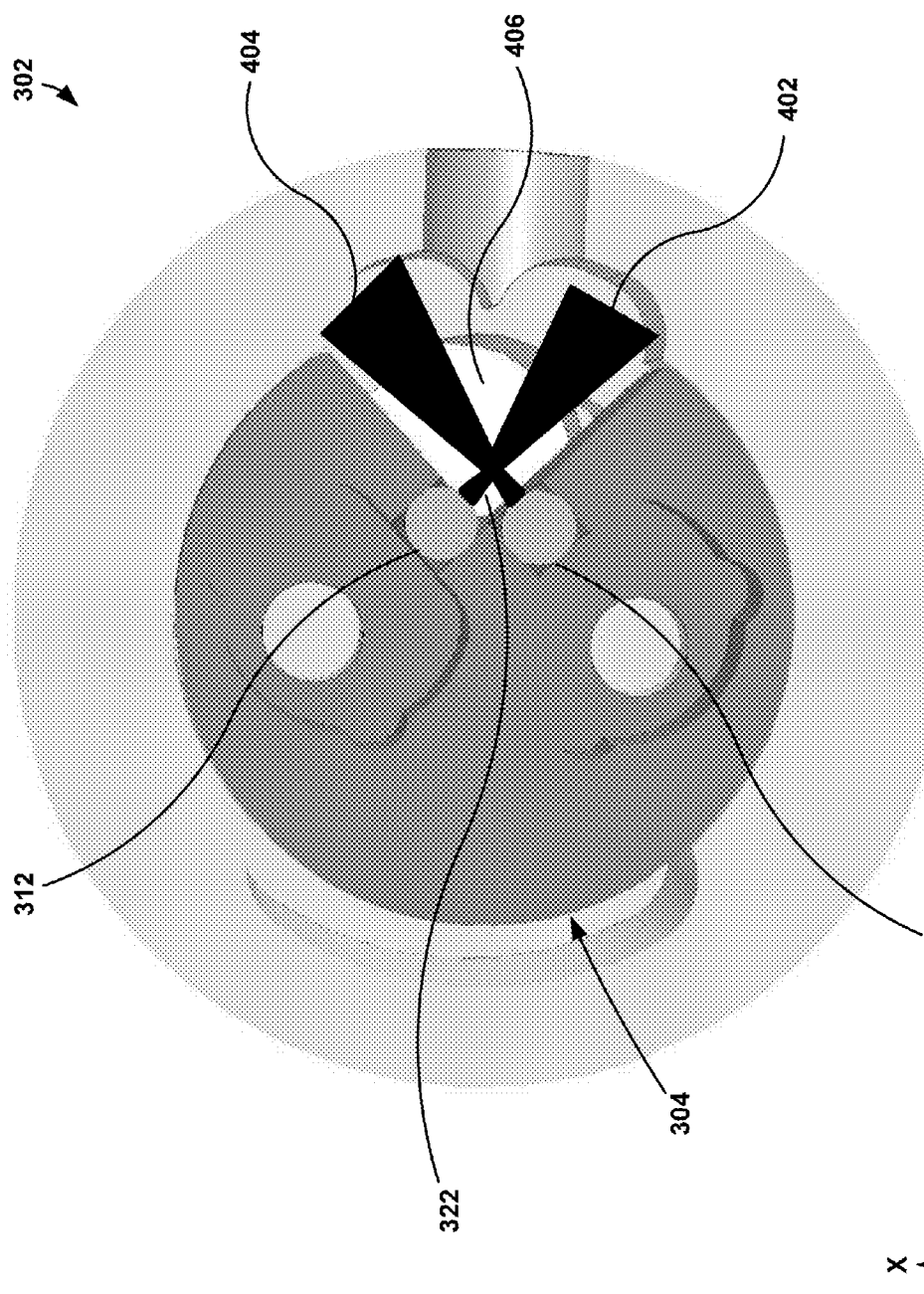

SELF-CLEANING OPTICAL SENSOR

TECHNICAL FIELD

This disclosure relates to optical sensors and, more particularly, to optical sensor fluid control.

BACKGROUND

Aqueous chemical solutions are used in a variety of situations. For example, in different applications, aqueous cleaning solutions are used to clean, sanitize, and/or disinfect kitchens, bathrooms, schools, hospitals, factories, and other similar facilities. Aqueous cleaning solutions typically include one or more chemical species dissolved in water. The chemical species impart various functional properties to the water such as cleaning properties, antimicrobial activity, and the like. Measuring the concentration of the chemical species in the aqueous solution before use can be beneficial to understand the properties of the solution and to determine if adjustment is required. For example, chemical solution monitoring can be especially useful in many industrial applications. In some cases, substantially real-time monitoring is used to determine a concentration of a chemical in a cleaning solution and then to adjust the chemical concentration during a short period of cleaning. In other cases, measurements may be taken on a periodic basis to maintain a nominal chemical concentration in the solution during a comparatively long period of operation.

An optical sensor is one type of device that can be used to analyze a chemical solution. The optical sensor may direct light through an optical window into a fluid solution and receive light from the fluid through an optical window. The optical sensor may direct and receive light through the same optical window or different optical windows. In either case, the optical sensor may determine a characteristic of the fluid solution based on the light received from the fluid solution. For example, the optical sensor may determine a concentration of a chemical species in the fluid based on the wavelength and/or magnitude of light received from the fluid.

In some applications, an optical sensor may be used to determine a characteristic of a fluid that contains a fouling material. In such a situation, an optical window of the optical sensor may become fouled, restricting the amount of light directed and/or received through the optical window. When light is restricted, the optical sensor may not determine a characteristic of the fluid solution as accurately as when the optical window is comparatively cleaner. For example, the optical sensor may attribute a reduced magnitude of received light from the fluid solution as being indicative of the fluid solution having a lower concentration of a chemical species rather than attribute the reduced amount of light to fouling interference.

SUMMARY

In general, this disclosure is directed towards optical sensors and optical-based techniques for determining a characteristic of a fluid such as, e.g., an aqueous chemical solution. In some examples, the optical sensor includes a flow chamber and a sensor head that is configured to be inserted into the flow chamber. The sensor head may determine a characteristic of a fluid as the fluid flows through the flow chamber. For example, the sensor head may optical analyze a fluid to determine a concentration of a chemical species in the fluid.

When the optical sensor is used to analyze fluid that contains fouling material, the fouling material may deposit within the optical sensor. If the fouling material accumulates within the optical sensor, the fouling material may reduce or fully block light from being transmitted to, or received from, the fluid by the optical sensor. When this occurs, the optical sensor may not be able to optical analyze the fluid with the accuracy demanded by some applications.

In some examples in accordance with this disclosure, a optical sensor is described that includes a flow chamber having an inlet port for receiving fluid for optical analysis by a sensor head. The inlet port may define a fluid nozzle that is configured to direct fluid entering the flow chamber against an optical window of the sensor head. In operation, fluid may travel through the inlet port and discharge from the fluid nozzle so as to impact the optical window of the sensor. The force of the incoming fluid impacting against the optical window may prevent fouling material from accumulating on the optical window and/or help remove accumulated fouling material from the optical window.

In one example, an optical sensor is described that includes a sensor head and a flow chamber. The sensor head includes a first optical window, a second optical window, at least one light source, and at least one detector. The at least one light source is configured to emit light through the first optical window into a flow of fluid and the at least one detector is configured to detect fluorescent emissions through the second optical window from the flow of fluid. In addition, in this example, the flow chamber includes a housing defining a cavity into which the sensor head is inserted, an inlet port configured to communicate the flow of fluid from outside of the cavity to an interior of the cavity, and an outlet port configured to communicate the flow of fluid from the interior of the cavity to back outside of the cavity. According to the example, the inlet port defines a first fluid nozzle configured to direct a portion of the flow of fluid against the first optical window and a second fluid nozzle configured to direct a portion of the flow of fluid against the second optical window.

In another example, a method is described that includes directing fluid through a first fluid nozzle of a flow chamber against a first optical window of a sensor head and directing fluid through a second fluid nozzle of the flow chamber against a second optical window of the sensor head. In the example, the sensor head includes at least one light source configured to emit light through the first optical window into a flow of fluid and at least one detector configured to detect fluorescent emissions through the second optical window from the flow of fluid.

In another example, an optical sensor system is described that includes an optical sensor, a liquid source, a gas source, and a controller. The optical sensor includes a sensor head with an optical window, at least one light source configured to emit light through the optical window into a flow of fluid, and at least one detector configured to detect fluorescent emissions through the optical window from the flow of fluid. The optical sensor also includes a flow chamber with a housing defining a cavity into which the sensor head is inserted, an inlet port is configured to communicate the flow of fluid from outside of the cavity to an interior of the cavity, and an outlet port configured to communicate the flow of fluid from the interior of the cavity to back outside of the cavity. The inlet port defines a fluid nozzle configured to direct the flow of fluid against the optical window. According to the example, the liquid source is configured to supply the flow of fluid communicating through the inlet port and the gas source is also configured to supply the flow of fluid communicating through the inlet port. The example further specifies that the controller is configured to control the gas source to place the gas source in fluid communication with the flow chamber so as to evacuate the flow chamber of liquid, and control the liquid source so as to place the liquid source in fluid communication with the flow chamber so as to direct liquid through the fluid nozzle, through a space of the flow chamber evacuated of liquid, and against the optical window.

In another example, a method is described that includes evacuating a flow chamber of an optical sensor of liquid, where the optical sensor includes a sensor head having an optical window that is inserted into the flow chamber, and the flow chamber includes an inlet port defining a fluid nozzle configured to direct fluid against the optical window. The method also includes flowing liquid through the inlet port of the flow chamber so as to direct liquid through the fluid nozzle, through a space of the flow chamber evacuated of liquid, and against the optical window.

The details of one or more examples are set forth in the accompanying drawings and the description below. Other features, objects, and advantages will be apparent from the description and drawings, and from the claims.

BRIEF DESCRIPTION OF DRAWINGS

FIG. 10 is another cross-sectional top view of the example flow chamber of FIG. 7, shown with a sensor head inserted into the chamber, taken along the A-A cross-section line indicated on FIG. 7.

DETAILED DESCRIPTION

Figure 1:
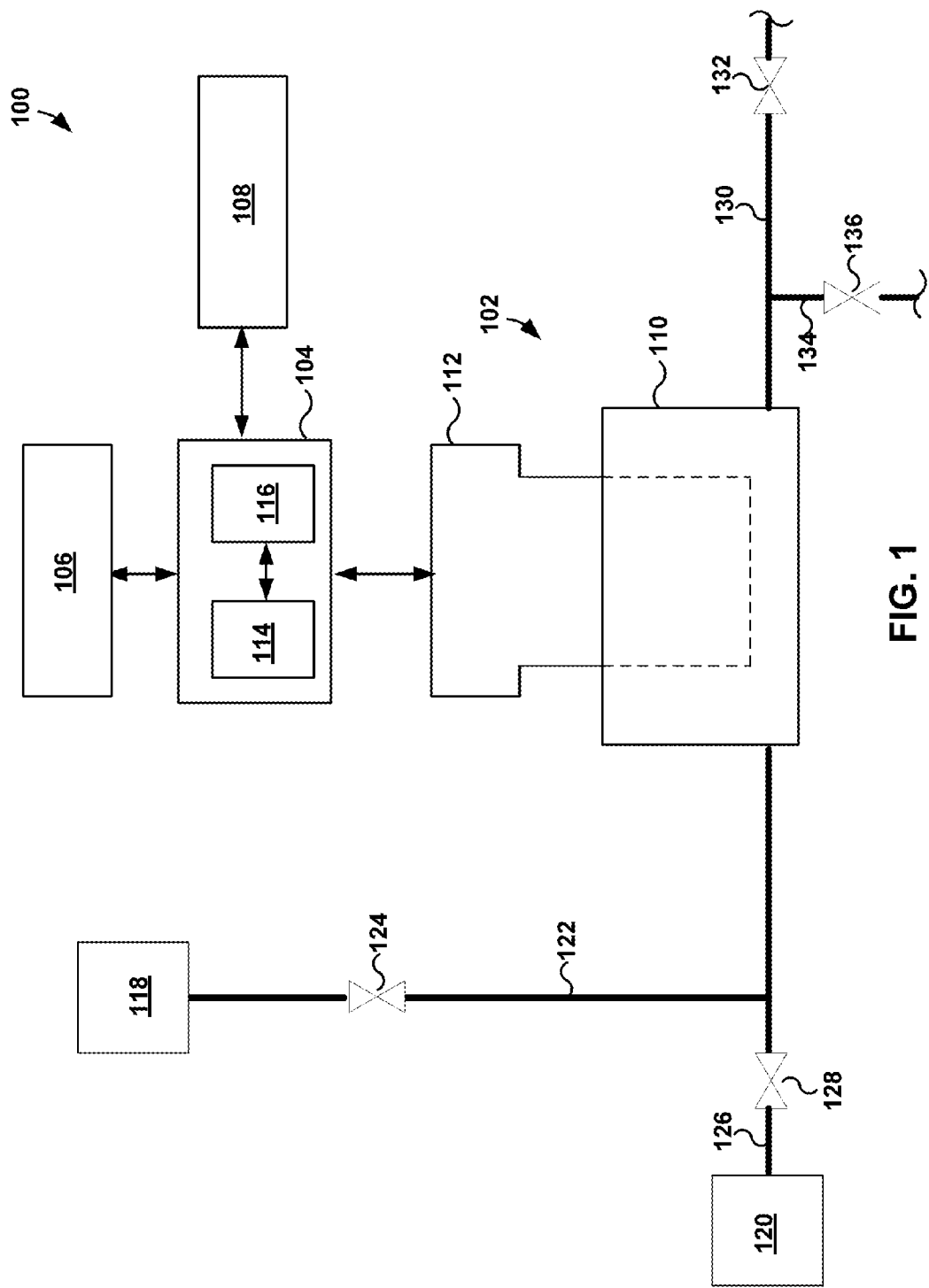
FIG. 1 is a diagram illustrating an example optical sensor system that includes an optical sensor according to examples of the disclosure.

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Fluids with active chemical agents are used in a variety of different industries for a variety of different applications. For example, in the cleaning industry, fluid solutions that include chlorine or other active chemical agents are often used to clean and disinfect various surfaces and equipment. In these solutions, the concentration of the active chemical agent or other parameters can affect the cleaning and disinfecting properties of the fluid. Accordingly, ensuring that a fluid is appropriately formulated and prepared for an intended application can help ensure that the fluid provides suitable cleaning and disinfecting properties in subsequent use.

This disclosure describes an optical sensor for determining a characteristic of a fluid medium. In particular, this disclosure describes methods, systems, and apparatuses related to an optical sensor that may be used to determine a characteristic of a fluid medium such as, e.g., a concentration of a chemical species in the fluid medium, a temperature of the fluid medium, or the like. Depending on the application, the optical sensor may be implemented as an online sensor that receives a flow of fluid from a fluid source on a continuous or periodic basis and analyzes the fluid to determine the characteristic in substantially real-time. For example, the optical sensor may be connected to a flow of fluid via a pipe, tube, or other conduit. The optical sensor may then receive a sample of the fluid from the source via the conduit and analyze the fluid to determine the characteristics of the fluid.

Depending on the application, the optical sensor may receive a fluid that contains fouling materials (e.g., solids particles) for optical analysis. As the fluid passes through the optical sensor, the fouling materials may deposit on the sensor, generating scaling or a film of accumulated fouling material. Over time, the amount of fouling material deposited on the sensor may increase until the sensor is no longer able to accurately optically analyze fluid passing through the sensor. For example, when the optical sensor includes an optical window for transmitting light into and/or receiving light from a fluid under analysis, the optical window may become covered with a layer of fouling material that restricts light passage through the optical window. This may cause the optical sensor to provide an inaccurate reading for the fluid characteristic intended to be determined by the sensor.

In accordance with the techniques described in this disclosure, an optical sensor with an inlet port that defines a fluid nozzle is provided. The fluid nozzle may be arranged to direct fluid entering the optical sensor against an optical window of the sensor. For example, the fluid nozzle may direct fluid entering the optical sensor directly against the optical window so that incoming fluid contacts the optical window of the sensor before contacting any other structure within the sensor. The force of the incoming fluid contacting the optical window may help inhibit fouling material from accumulating on the optical window and/or flush away accumulated fouling material. Instead of having to regularly remove the optical sensor from operation for cleaning, the fluid directed against the optical window may perform a self-cleaning function. As a result, the optical sensor may remain in service without requiring cleaning and/or optical sensor may exhibit an extended service life between cleanings.

In some examples according to this disclosure, the optical sensor includes at least a first optical window through which a light source of the sensor emits light into a fluid and a second optical window through which a detector of the sensor receives light from the fluid. The sensor may emit light into the fluid to generate fluorescent emissions and the detector may detect the fluorescent emissions for determining a characteristic of the fluid. In this example, the optical sensor may include a first fluid nozzle configured to direct a portion of an incoming fluid flow against the first optical window and a second fluid nozzle configured to direct a different portion of the incoming fluid flow against the second optical window. By providing a separate nozzle associated with each optical window, each optical window may be impacted with higher pressure fluid streams than if the optical sensor employs a single nozzle for multiple optical windows. This may improve the cleaning action of the incoming fluid stream.

In some instances when an optical sensor according to the disclosure is used as part of a system, the optical sensor may be fluidly connected to both a liquid source that supplies a flow of incoming fluid to the sensor as well as a gas source that can supply a flow of incoming fluid. During operation, the liquid source may supply fluid to the optical sensor for analysis. Periodically, however, the liquid source may be closed and the gas source opened so that the optical sensor is evacuated of liquid and filled with gas. Thereafter, the liquid source may be reopened to refill the optical sensor with liquid for analysis. When this occurs, the liquid initially entering the optical sensor may travel through the gas space in the optical sensor more rapidly than if the optical sensor were filed with liquid. Consequently, the initial incoming liquid may impact the optical window of the sensor with more force than liquid subsequently entering the sensor when the sensor is already filled with liquid. This may provide a comparatively high pressure cleaning action that helps remove accumulated fouling material from the optical window.

FIG. 1 is a conceptual diagram illustrating an example optical sensor system 100, which may be used to analyze a chemical solution having fluorescent properties. System 100 includes an optical sensor 102, a controller 104, a power supply 106, and a user interface 108. Optical sensor 102 includes a flow chamber 110 that defines a cavity for receiving and containing a flow of fluid and a sensor head 112 that is inserted into the flow chamber. Sensor head 112 is configured to determine one or more characteristics of a fluid as the fluid passes through flow chamber 110 such as, e.g., a concentration of a chemical compound in the fluid, a temperature of the fluid, or the like. Optical sensor 102 can communicate with controller 104 in operation, and controller 104 can control optical sensor system 100.

Controller 104 is communicatively connected to optical sensor 102 and includes a processor 114 and a memory 116. Signals generated by optical sensor 102 are communicated to controller 104 via a wired or wireless connection, which in the example of FIG. 1 is illustrated as wired connection. Memory 116 stores software for running controller 104 and may also store data generated or received by processor 114, e.g., from optical sensor 102. Processor 114 runs software stored in memory 116 to manage the operation of optical sensor 102.

Flow chamber 110 of optical sensor 102 includes an inlet port for communicating fluid from outside of the flow chamber to an interior of the flow chamber as well as an outlet port for discharging the fluid back outside of the flow chamber. Sensor head 112 is inserted (e.g., removably or permanently) into flow chamber 110 and includes at least one optical window for directing light into fluid passing through flow chamber 110 and/or receiving optical energy from the flow of fluid. In operation, fluid enters flow chamber 110 and is directed past the optical window of sensor head 112. Once inside the flow chamber, sensor head 112 may optically analyze the fluid as the fluid moves past the optical window. For instance, when optical sensor 102 is implemented as a fluorometer, the optical sensor may direct light into the fluid to generate fluorescent emissions and then detect the fluorescent emissions to optically analyze the fluid.

As described in greater detail below (FIGS. 7-10), flow chamber 110 may include an inlet that defines a fluid nozzle configured to direct fluid entering the flow chamber directly against the optical window of the sensor head. For example, flow chamber 110 may include a fluid nozzle that is in the same plane as the optical window of the sensor head and oriented so that fluid entering the flow chamber directly contacts the optical window after discharging from the fluid nozzle. Instead of contacting a wall surface or other internal surface of flow chamber 110 after discharging from the fluid nozzle, the fluid nozzle may discharge fluid so that the fluid contacts the optical window of sensor head 112 before contacting any other surface within the flow chamber. In some examples, the flow nozzle is oriented so that a center of the fluid flow emitted by the fluid nozzle is directed at approximately a center of the optical window. Directing fluid entering flow chamber 110 against the optical window of sensor head 112 may help reduce or eliminate fouling build-up on the optical window.

Optical sensor 102 is connected to at least one fluid source which, in the example of FIG. 1, is illustrated as two fluid sources (a first fluid source 118 and a second fluid source 120). First fluid source 118 is in fluid communication with flow chamber 110 via a first fluid conduit 122 which passes through a first valve 124. Second fluid source 120 is in fluid communication with flow chamber 110 via a second fluid conduit 126 which passes through a second valve 128. First fluid conduit 122 and second fluid conduit 126 are fluidly connected to a common inlet port (e.g., a single inlet port) of flow chamber 110 in the example of optical sensor system 100. In other examples, such as examples where flow chamber 110 includes multiple inlet ports, first fluid conduit 122 and second fluid conduit 126 may be fluidly connected to the flow chamber through different inlet ports.

Although not illustrated in FIG. 1, controller 104 may be communicatively coupled to first valve 124 and second valve 128. In some examples, controller 104 selectively opens and closes first valve 124 and second valve 128 so as to place fluid from first fluid source 118 and/or second fluid source 120 in fluid communication with flow chamber 110. For example, memory 116 may store instructions that, when executed by processor 114, cause controller 104 to selectively open and/or close first valve 124 and/or second valve 128 so as to selectively place fluid from first fluid source 118 and/or second fluid source 120 in fluid communication with flow chamber 110. When first fluid source 118 is in fluid communication with flow chamber 110, fluid from the first fluid source can flow through the flow chamber. By contrast, when second fluid source 120 is in fluid communication with flow chamber 110, fluid from the second fluid source can flow through the flow chamber.

In addition to or in lieu of controlling first valve 124 and second valve 128, controller 104 may be communicatively coupled to one or more delivery devices that control delivery of fluid from first fluid source 118 and second fluid source 120. Example delivery devices include pumps and other metering devices. Controller 104 may start and/or stop the delivery devices to place fluid from first fluid source 118 and/or second fluid source 120 in fluid communication with flow chamber 110. Controller 104 may also increases and/or decreases the rate of the delivery devices to adjust the rate at which fluid from first fluid source 118 and/or second fluid source 120 enters flow chamber 110.

First fluid source 118 and second fluid source 120 may each provide gaseous fluids, liquid fluids, or one fluid source may provide a gaseous fluid while another fluid source provides a liquid fluid. In one example, first fluid source 118 is a gaseous fluid source and second fluid source 120 is a liquid fluid source. Second fluid source 120 may supply a liquid to flow chamber 110 that is intended for optical analysis by sensor head 112. For example, second fluid source 120 may supply a liquid to flow chamber 110 that includes a chemical compound that imparts functional properties to the liquid (e.g., cleaning properties, antimicrobial properties). Optical sensor 102 may receive the liquid and optically analyze the liquid to determine the concentration of the chemical compound, e.g., to monitor and/or adjust the composition of the liquid source. First fluid source 118 may supply a gas to flow chamber 110 that, in some examples, is used for cleaning the flow chamber and/or purging the flow chamber of liquid.

During operation of optical sensor 102, second fluid source 120 may supply liquid to flow chamber 110 for optical analysis that contains fouling materials (e.g., solids particles). As the liquid passes through the flow chamber, the fouling materials may accumulate within the flow chamber and deposit on sensor head 112. Over time, the fouling materials may buildup on sensor head 112 to a level where optical sensor 102 in no longer able to accurately determine a characteristic of a liquid passing through the flow chamber.

To help reduce or eliminate fouling accumulation within optical sensor 102, first fluid source 118 may periodically supply gas to flow chamber 110 to purge the flow chamber of liquid. For example, controller 104 may control first valve 124 and second valve 128 during operation of optical sensor system 100 to stop liquid flow to the flow chamber and initiate gas flow to flow chamber 110. The gas may displace the liquid in flow chamber 110 so that the flow chamber is evacuated of liquid. Thereafter, controller 104 may resume fluid communication between the liquid fluid source and flow chamber. Liquid entering the gas filled flow chamber 110 may travel at a higher velocity within the chamber than when the chamber is filled with fluid. This high velocity fluid entering flow chamber 110 may help remove accumulated fouling material from within flow chamber 110 such as, e.g., fouling on an optical window of sensor head 112.

For instance, during operation of an optical sensor that includes a flow chamber 110 having a fluid nozzle configured to direct fluid against an optical window (e.g., FIGS. 7-10), liquid may discharge from the fluid nozzle against an optical window of sensor head 112. This may occur when flow chamber 110 is in fluid communication with a liquid fluid source, such as second fluid source 120. Periodically, controller 104 may close second valve 128 to block fluid communication between the liquid second fluid source 120 and flow chamber 110 and also open first valve 124 to place the gaseous first fluid source 118 in fluid communication with the flow chamber. The gas from first fluid source 118 may displace the liquid fluid within flow chamber 110 so the flow chamber is filled with gaseous fluid rather than liquid fluid. Controller 104 may subsequently close first fluid valve 124 to block fluid communication between the gaseous first fluid source 118 and flow chamber 110 and also open second valve 128 to place liquid second fluid source 120 in fluid communication with the flow chamber. As liquid initially enters flow chamber 110 to refill the flow chamber, the liquid may discharge from a fluid nozzle of flow chamber 110 and travel through a gas filled space before impacting an optical window of sensor head 112. This liquid traveling through the gas filled space may travel faster than if the liquid was traveling through the same space and the space was filled with liquid. For example, the liquid traveling through the gas filled space may travel at least twice as fast (e.g., at least three times as fast, between approximately 3 and approximately 5 times as fast) as if the liquid was traveling through the same space and the space was filled with liquid. As a result, the liquid may carry more force for removing accumulated fouling material from an optical window of sensor head 112 than if flow chamber 110 is not evacuated of liquid.

Independent of the specific configuration of flow chamber 110, controller 104 of optical sensor system 100 may control first fluid source 118 and second fluid source 120 to alternately place one of the fluid sources in communication with flow chamber 110 with any suitable frequency. In one example, controller 104 close first valve 124 to block fluid communication between the gaseous first fluid source 118 and flow chamber 110 and also opens second valve 128 to open fluid communication between the liquid second fluid source 120 and the flow chamber. Controller 104 may hold first valve 124 closed and second valve 128 open, allowing liquid fluid to flow into and through flow chamber 110, for a period of greater than approximately 30 seconds such as, e.g., greater than 1 minute, greater than 5 minutes, greater than 1 hour, or a period ranging from approximately 1 minute to approximately 5 minutes. Controller 104 may subsequently close second valve 128 to block fluid communication between the liquid second fluid source 120 and flow chamber 110 and open first valve 124 to open fluid communication between the gaseous first fluid source 118 and the flow chamber. Controller 104 may then hold first valve 124 open and second valve 128 closed, for a period of greater than 10 seconds such as, e.g., greater than 1 minute, greater than 10 minutes, or a period ranging from approximately 1 minute to approximately 30 minutes. The foregoing values are merely examples, and other ranges of time are both possible and contemplated.

In some examples, controller 104 controls the supply of gaseous fluid and liquid fluid to flow chamber 110 so a ratio of the amount of time the flow chamber is filled with gas divided by the amount of time the flow chamber is filled with liquid is greater than 1. For example, controller 104 may control the supply of gaseous fluid and liquid fluid to flow chamber 110 so that the ratio of the amount of time the flow chamber is filled with gas divided by the amount of time the flow chamber is filled with liquid is greater than 2, greater than 5, greater than 10, or between 2 and 10. In such examples, flow chamber 110 may be filled with gas for a longer period of time than the flow chamber is filled with liquid. In instances in which the liquid received by flow chamber 110 contains fouling material, reducing the amount of time the liquid passes through the flow chamber may reduce the amount of fouling material deposited within the chamber. Instead of allowing flow chamber 110 to remain filled with liquid fluid that may contain fouling material, the flow chamber can instead be evacuated of liquid and filled with gas. Flow chamber 110 may periodically be filled with liquid for analysis and then refilled with gas, which may extend the length of time that optical sensor 102 can remain in service before needing to be removed for cleaning.

After passing through the flow chamber 110, fluid may be returned to a fluid source or discarded. In the example of FIG. 1, flow chamber 110 is in fluid communication with an outlet conduit 130 via an outlet valve 132 and a drain conduit 134 via a drain valve 136. In operation, controller 104 may be communicatively coupled to outlet valve 132 and drain valve 136 for selectively opening and closing the valves. For example, controller 104 may control outlet valve 132 to open the valve and drain valve 136 to close the valve when first valve 124 is closed and second valve 128 is opened. This may allow fluid to flow from second fluid source 120, through flow chamber 110, and return to the fluid source via outlet conduit 130. Conversely, controller 104 may control outlet valve 132 to close the valve and drain valve 136 to open the valve when first valve 124 is opened and second valve 128 is closed. This may allow fluid to flow out of flow chamber 110 (e.g., for evacuating the chamber of liquid) and/or provide a separate fluid pathway for discharging accumulated fouling material flushed out of the flow chamber.

First fluid source 118 and second fluid source 120 may each be any suitable type of fluid. In examples in which first fluid source 118 is a gaseous fluid, the gas may be atmospheric air, oxygen, nitrogen, carbon dioxide, or any other acceptable type of gas. In some examples, the gas is at atmospheric pressure. In other examples, the gas is at a positive pressure relative to atmospheric pressure. In addition, in examples in which second fluid source 120 is a liquid fluid, the fluid may be a liquid that is intended to be optically analyzed (e.g., to determine a concentration of a chemical compound in the liquid) or a liquid that is provided to clean optical sensor 102. For example, second fluid source 120 may be water or another cleaning fluid for cleaning fouling material from optical sensor 102. In other examples, the liquid intended to be optically analyzed may directed against an optical window of sensor head 112 in addition to or in lieu of providing a separate cleaning liquid. That is, instead of supplying a separate cleaning liquid to optical sensor 102 for removing fouling material from the sensor, liquid entering the optical sensor for analysis may itself be directed into the sensor in such a way as to help reduce or eliminate fouling accumulation within the sensor. While optical sensor system 100 in the example of FIG. 1 includes a first fluid source 118 and a second fluid source 120, in other examples, an optical sensor system may include fewer fluid sources (e.g., a single fluid source) or more fluid source (e.g., three, four, or more fluid sources) and the disclosure is not limited in this respect.

For instance, in one example optical sensor system 100 includes a gaseous fluid source, a source of liquid fluid for cleaning optical sensor 102, and a source of liquid fluid to be analyzed by optical sensor 102. Controller 104 can control the system to place the gaseous fluid source in fluid communication with flow chamber 110 while fluid communication between the source of liquid fluid for cleaning and the source of liquid fluid to be analyzed is blocked. This may evacuate flow chamber 110 of liquid. Thereafter, controller 104 can control the system to place the source of liquid fluid for cleaning flow chamber 110 in fluid communication with flow chamber 110 while flow to the gaseous fluid source and the source of liquid fluid to be analyzed is blocked. Controller 104 can subsequently control the system to place the source of liquid fluid to be analyzed in fluid communication with flow chamber 110 while fluid communication between the source of liquid fluid for cleaning and the source of liquid fluid to be analyzed is blocked.

Optical sensor 102 in optical sensor system 100 can be used to analyze a variety of different types of liquid fluids. Example fluids that may be analyzed by optical sensor 102 include, but are not limited to, cleaning agents, sanitizing agents, cooling water for industrial cooling towers, biocides such as pesticides, anti-corrosion agents, anti-scaling agents, anti-fouling agent, laundry detergents, clean-in-place cleaners, floor coatings, vehicle care compositions, water care compositions, bottle washing compositions, and the like. In some examples, the fluid is an aqueous chemical solution that includes one or more chemical additives. These or other fluids may be used as second fluid source 120.

In some examples, optical sensor 102 is configured as a fluorometer with a light source that emits optical energy into fluid flowing through flow chamber 110. The fluid may emit fluorescent radiation in response to the optical energy directed into the fluid. The optical sensor 102 may then detect the emitted fluorescent radiation and determine various characteristics of the solution, such as a concentration of one or more chemical compounds in the solution, based on the magnitude of the emitted fluorescent radiation. In order to enable optical sensor 102 to detect fluorescent emissions, liquid fluid provided from a fluid source in these examples may include a molecule that exhibits fluorescent characteristics. In some examples, the fluid may include a polycyclic compound and/ or a benzene molecule that has one or more substituent electron donating groups such as, e.g., —OH, —NH$_2$, and —OCH$_3$, which may exhibit fluorescent characteristics. Depending on the application, these compounds may be naturally present in the fluid entering optical sensor 102 because of the functional properties (e.g., cleaning and sanitizing properties) imparted to the fluids by the compounds.

In addition to or in lieu of a naturally fluorescing compound, the liquid fluid may include a fluorescent tracer (which may also be referred to as a fluorescent marker). The fluorescent tracer can be incorporated into the fluid specifically to impart fluorescing properties to the fluid. Example fluorescent tracer compounds include, but are not limited to naphthalene disulfonate (NDSA), 2-naphthalenesulfonic acid, Acid Yellow 7,1,3,6,8-pyrenetetrasulfonic acid sodium salt, and fluorescein.

Independent of the specific composition of the fluid received by flow chamber 110, optical sensor 102 can determine one or more characteristics of the fluid flowing through flow chamber. Example characteristics include, but are not limited to, the concentration of one or more chemical compounds within fluid, the temperature of the fluid, and/or other characteristics of the fluid may help ensure that the fluid is appropriately formulated for an intended application. Optical sensor 102 may communicate detected characteristic information to controller 104.

While optical sensor 102 within system 100 is generally described as receiving a flow of moving fluid that passes through the optical sensor, in other examples, the optical sensor may be used to determine one or more characteristics of a stationary volume of fluid that does not flow through a flow chamber of the optical sensor. When optical sensor 102 includes a flow chamber with inlet and outlet ports (FIGS. 7-10), the inlet and outlet ports may be plugged to created a bounded cavity for holding a stationary (e.g., non-flowing) volume of fluid. A bounded flow chamber may be useful for calibrating optical sensor 102. During calibration, the flow chamber can be filled with a fluid having known characteristics (e.g., a known concentration of one or more chemical compounds, a known temperature), and optical sensor 102 can determine estimated characteristics of the calibration solution. The estimated characteristics determined by the optical sensor can be compared to the known characteristics (e.g., by controller 104) and used to calibrate optical sensor 102.

Optical sensor system 100 in the example of FIG. 1 also includes power supply 106, user interface 108, and conduits 122, 126, 130, 134. Power supply 106 delivers operating power to the various components of optical sensor system 100 and, in different examples, may include power from a supply line, such as an alternating current or direct current supply line, or a battery. User interface 108 can be used to provide input to optical sensor system 100 (e.g., for changing operating parameters of the system, running a calibration routine) or to receive output from the system. User interface 108 may generally include a display screen or other output media, and user input media. In some examples, optical sensor system 100 can communicate via a wired or wireless connection with one or more remote computing devices. Fluid conduits 122, 126, 130, 134 in system 100 may be any type of flexible or inflexible tubing, piping, or other fluid pathway.

Figure 2:
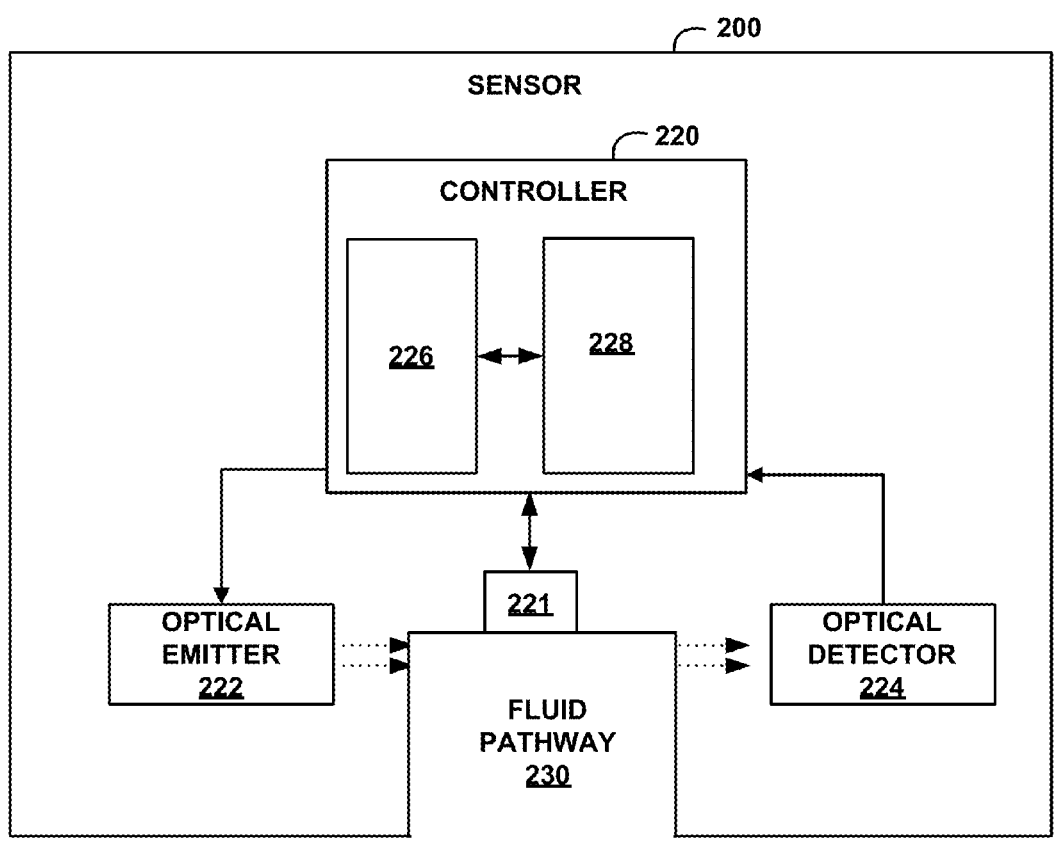
FIG. 2 is a block diagram illustrating an example optical sensor that may be used in the example system of FIG. 1.

In the example of FIG. 1, optical sensor 102 determines a characteristic of the fluid flowing through flow chamber 110 (e.g., a concentration of a chemical compound, a temperature, or the like). FIG. 2 is block diagram illustrating an example of an optical sensor 200 that determines a characteristic of a fluid medium. Sensor 200 may be used as optical sensor 102 in optical sensor system 100, or sensor 200 may be used in other applications beyond optical sensor system 100.

With reference to FIG. 2, sensor 200 includes a controller 220, one or more optical emitters 222 (referred to herein as "optical emitter 222"), one or more optical detectors 224 (referred to herein as "optical detector 224"), and a temperature sensor 221. Controller 220 includes a processor 226 and a memory 228. In operation, optical emitter 222 directs light into fluid flowing through fluid channel 230 and optical detector 224 detects fluorescent emissions generated by the fluid. The light directed into the fluid by optical emitter 222 may generate fluorescent emissions by exciting electrons of fluorescing molecules within the fluid, causing the molecules to emit energy (i.e., fluoresce) that can be detected by optical detector 224. For example, optical emitter 222 may direct light at one frequency (e.g., ultraviolet frequency) into fluid flowing through fluid channel 230 and cause fluorescing molecules to emit light energy at a different frequency (e.g., visible light frequency). Temperature sensor 221 within sensor 200 can measure a temperature of fluid flow adjacent to (e.g., in contact with) the sensor. In some examples, sensor 200 communicates with external devices.

Memory 228 stores software and data used or generated by controller 220. For example, memory 228 may store data used by controller 220 to determine a concentration of one or more chemical components within the fluid being monitored by sensor 200. In some examples, memory 228 stores data in the form of an equation that relates fluorescent emissions detected by optical detector 224 to a concentration of one or more chemical components.

Processor 226 runs software stored in memory 228 to perform functions attributed to sensor 200 and controller 220 in this disclosure. Components described as processors within controller 220, controller 104, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

Optical emitter 222 includes at least one optical emitter that emits optical energy into a fluid present with fluid channel 230. In some examples, optical emitter 222 emits optical energy over range of wavelengths. In other examples, optical emitter 222 emits optical energy at one or more discrete wavelengths. For example, optical emitter 222 may emit at two, three, four or more discrete wavelengths.

In one example, optical emitter 222 emits light within the ultraviolet (UV) spectrum. Light within the UV spectrum may include wavelengths in the range from approximately 200 nm to approximately 400 nanometers. Light emitted by optical emitter 222 is directed into fluid within fluid channel 230. In response to receiving the optical energy, fluorescing molecules within the fluid may excite, causing the molecules to produce fluorescent emissions. The fluorescent emissions, which may or may not be at a different frequency than the energy emitted by optical emitter 222, may be generated as excited electrons within fluorescing molecules change energy states. The energy emitted by the fluorescing molecules may be detected by optical detector 224. For example, optical emitter 222 may emit light in the frequency range of approximately 280 nm to approximately 310 nm and, depending on the composition of the fluid, cause fluorescent emissions in the range of approximately 310 nm to approximately 400 nm.

Optical emitter 222 may be implemented in a variety of different ways within sensor 200. Optical emitter 222 may include one or more light sources to excite molecules within the fluid. Example light sources include light emitting diodes (LEDS), lasers, and lamps. In some examples, optical emitter 222 includes an optical filter to filter light emitted by the light source. The optical filter may be positioned between the light source and the fluid and be selected to pass light within a certain wavelength range. In some additional examples, the optical emitter includes a collimator, e.g., a collimating lens, hood or reflector, positioned adjacent the light source to collimate the light emitted from the light source. The collimator may reduce the divergence of the light emitted from the light source, reducing optical noise.

Sensor 200 also includes optical detector 224. Optical detector 224 includes at least one optical detector that detects fluorescent emissions emitted by excited molecules within fluid channel 230. In some examples, optical detector 224 is positioned on a different side of fluid channel 230 than optical emitter 222. For example, optical detector 224 may be positioned on a side of fluid channel 230 that is offset approximately 90 degrees relative to optical emitter 222. Such an arrangement may reduce the amount of light that is emitted optical emitter 222, transmitted through fluid within fluid channel 230, and detected by optical detector 224. This transmitted light can potentially cause interference with fluorescent emissions detected by the optical detector.

In operation, the amount of optical energy detected by optical detector 224 may depend on the contents of the fluid within fluid channel 230. If the fluid channel contains a fluid solution that has certain properties (e.g., a certain chemical compound and/or a certain concentration of a chemical species), optical detector 224 may detect a certain level of fluorescent energy emitted by the fluid. However, if the fluid solution has different properties (e.g., a different chemical compound and/or a different concentration of the chemical species), optical detector 224 may detect a different level of fluorescent energy emitted by the fluid. For example, if a fluid within fluid channel 230 has a first concentration of a fluorescing chemical compound(s), optical detector 224 may detect a first magnitude of fluorescent emissions. However, if the fluid within fluid channel 230 has second concentration of the fluorescing chemical compound(s) that is greater than the first concentration, optical detector 224 may detect a second magnitude of fluorescent emissions that is greater than the first magnitude.

Optical detector 224 may also be implemented in a variety of different ways within sensor 200. Optical detector 224 may include one or more photodetectors such as, e.g., photodiodes or photomultipliers, for converting optical signals into electrical signals. In some examples, optical detector 224 includes a lens positioned between the fluid and the photodetector for focusing and/or shaping optical energy received from the fluid.

Sensor 200 in the example of FIG. 2 also includes temperature sensor 221. Temperature sensor 221 is configured to sense a temperature of a fluid passing through a flow chamber of the sensor. In various examples, temperature sensor 316 may be a bi-metal mechanical temperature sensor, an electrical resistance temperature sensor, an optical temperature sensor, or any other suitable type of temperature sensor. Temperature sensor 221 can generate a signal that is representative of the magnitude of the sensed temperature. In other examples, sensor 200 does not include temperature sensor 221.

Controller 220 controls the operation of optical emitter 222 and receives signals concerning the amount of light detected by optical detector 224. Controller 220 also received signals from temperature sensor 221 concerning the temperature of the fluid in contact with the sensor. In some examples, controller 220 further processes signals, e.g., to determine a concentration of more or more chemical species within the fluid passing through fluid channel 230.

In one example, controller 220 controls optical emitter 222 to direct radiation into a fluid and further controls optical detector 224 to detect fluorescent emissions emitted by the fluid. Controller 220 then processes the light detection information to determine a concentration of a chemical species in the fluid. For example, in instances in which a fluid includes a fluorescent tracer, a concentration of a chemical species of interest can be determined based on a determined concentration of the fluorescent tracer. Controller 220 can determine a concentration of the fluorescent tracer by comparing the magnitude of fluorescent emissions detected by optical detector 224 from a fluid having an unknown concentration of the tracer to the magnitude of the fluorescent emissions detected by optical detector 224 from a fluid having an known concentration of the tracer. Controller 220 can determine the concentration of a chemical species of interest using Equations (1) and (2) below:

$$C_c = C_m \times \frac{C_o}{C_f} \quad \text{Equation 1}$$

$$C_m = K_m \times (S_x - Z_o) \quad \text{Equation 2}$$

In Equations (1) and (2) above, $C_c$ is a current concentration of the chemical species of interest, $C_m$ is a current concentration of the fluorescent tracer, $C_o$ is a nominal concentration of the chemical species of interest, $C_f$ is a nominal concentration of the fluorescent tracer, $K_m$ is a slope correction coefficient, $S_x$ is a current fluorescent measurement signal, and $Z_o$ is a zero shift. Controller 220 may further adjust the determined concentration of the chemical species of interest based on the temperature measured by temperature sensor 221.

Figure 3:
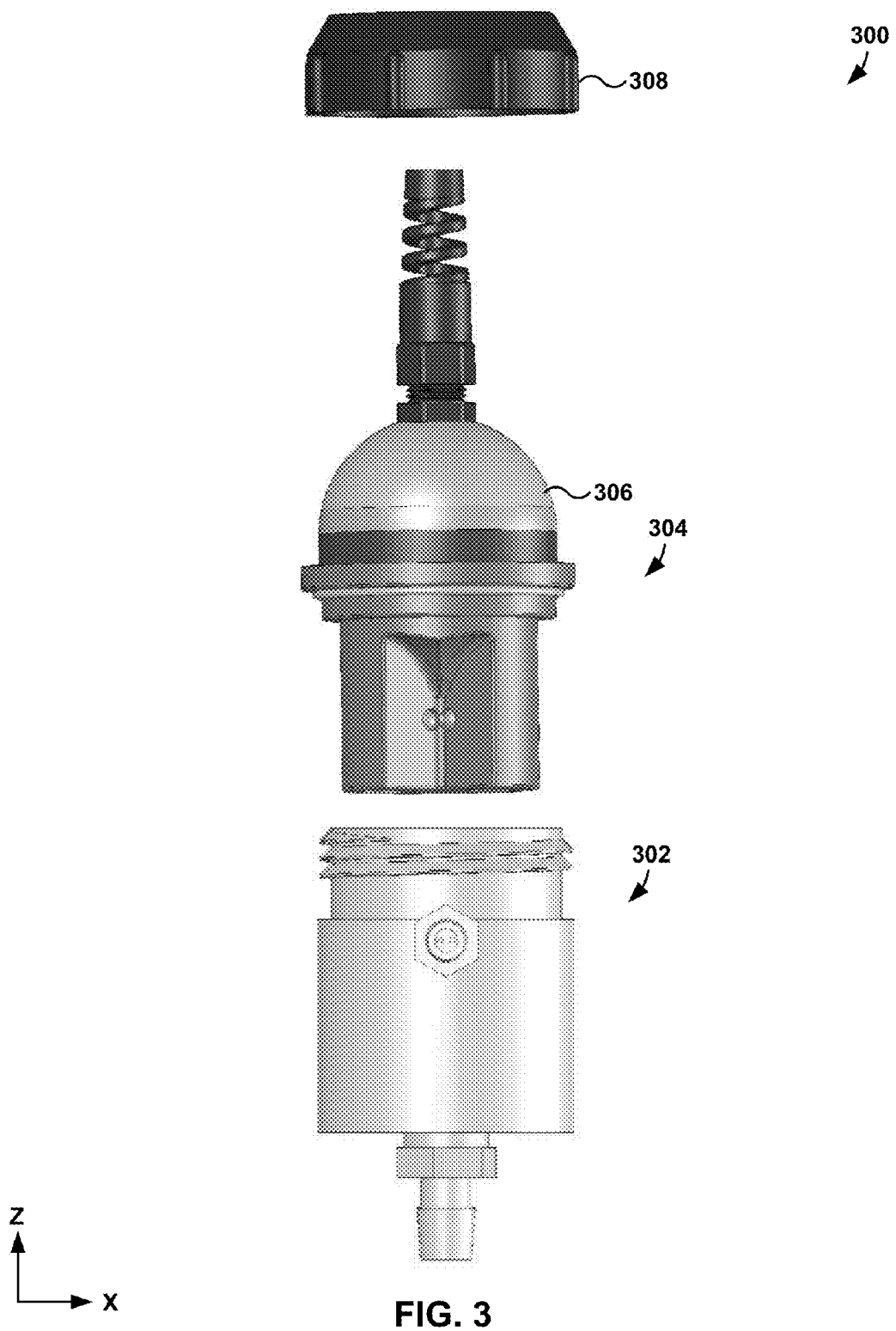
FIGS. 3 and 4 are schematic drawings of an example physical configuration of an optical sensor that may be used by the optical sensors in FIGS. 1 and 2.
Figure 4:
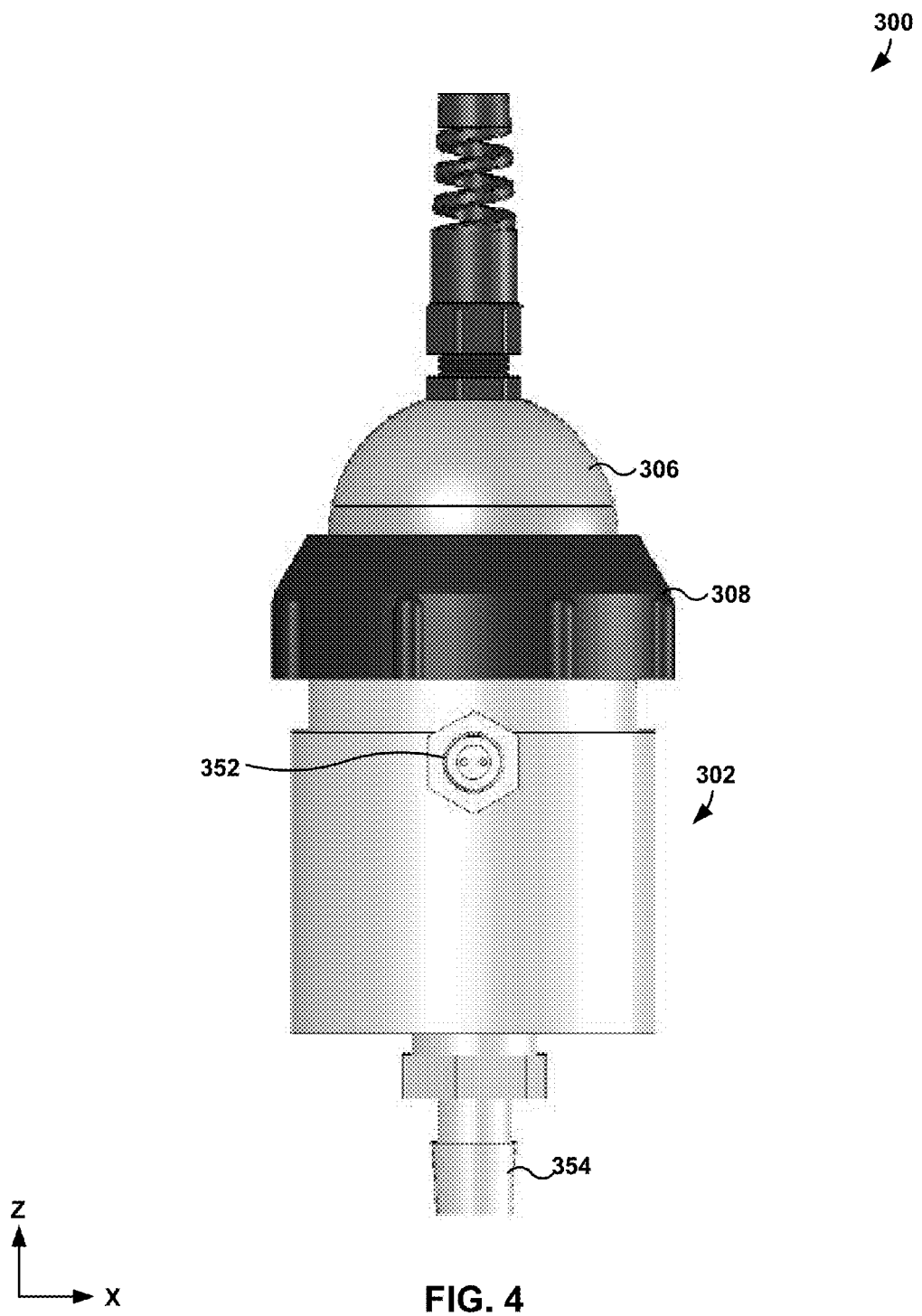

Sensor 102 (FIG. 1) and sensor 200 (FIG. 2) can have a number of different physical configurations. FIGS. 3 and 4 are schematic drawings of one example configuration of a sensor 300, which can be used by sensor 102 and sensor 200. Sensor 300 includes a flow chamber 302, a sensor head 304, a sensor cap 306, and a locking member 308. Sensor head 304 is shown outside of and insertable into flow chamber 302 in FIG. 3, while sensor head is shown inserted into flow chamber 302 and secured to the flow chamber via locking member 308 in FIG. 4. When sensor head 304 is inserted into and secured to flow chamber 302, the flow chamber may define a bounded cavity that receives fluids from a fluid source and controls fluid flow past sensor head 304. For example, as described in greater detail below, flow chamber 302 may include a fluid nozzle that directs fluid entering flow chamber 302 against an optical window of sensor head 304. The fluid nozzle may help avoid fouling accumulation on sensor head 304 and/or remove accumulated fouling material from the sensor head, e.g., when the sensor is implemented as an online sensor continuously receiving moving fluid from a fluid source.

Flow chamber 302 of sensor 300 is configured to receive and contain sensor head 304. In general, sensor head 304 may be any component of sensor 300 that is insertable into flow chamber 302 and configured to sense a characteristic of a fluid within the fluid chamber. In various examples, sensor head 304 may be configured to sense characteristics for determining a concentration of one or more chemical compounds within the fluid in flow chamber 302, a temperature of the fluid in the fluid chamber, the pH of the fluid in the fluid chamber, and/or other characteristics of the fluid may help ensure that the fluid is appropriately formulated for an intended application, as described above with respect to FIGS. 1 and 2.

Figures 5, 6:
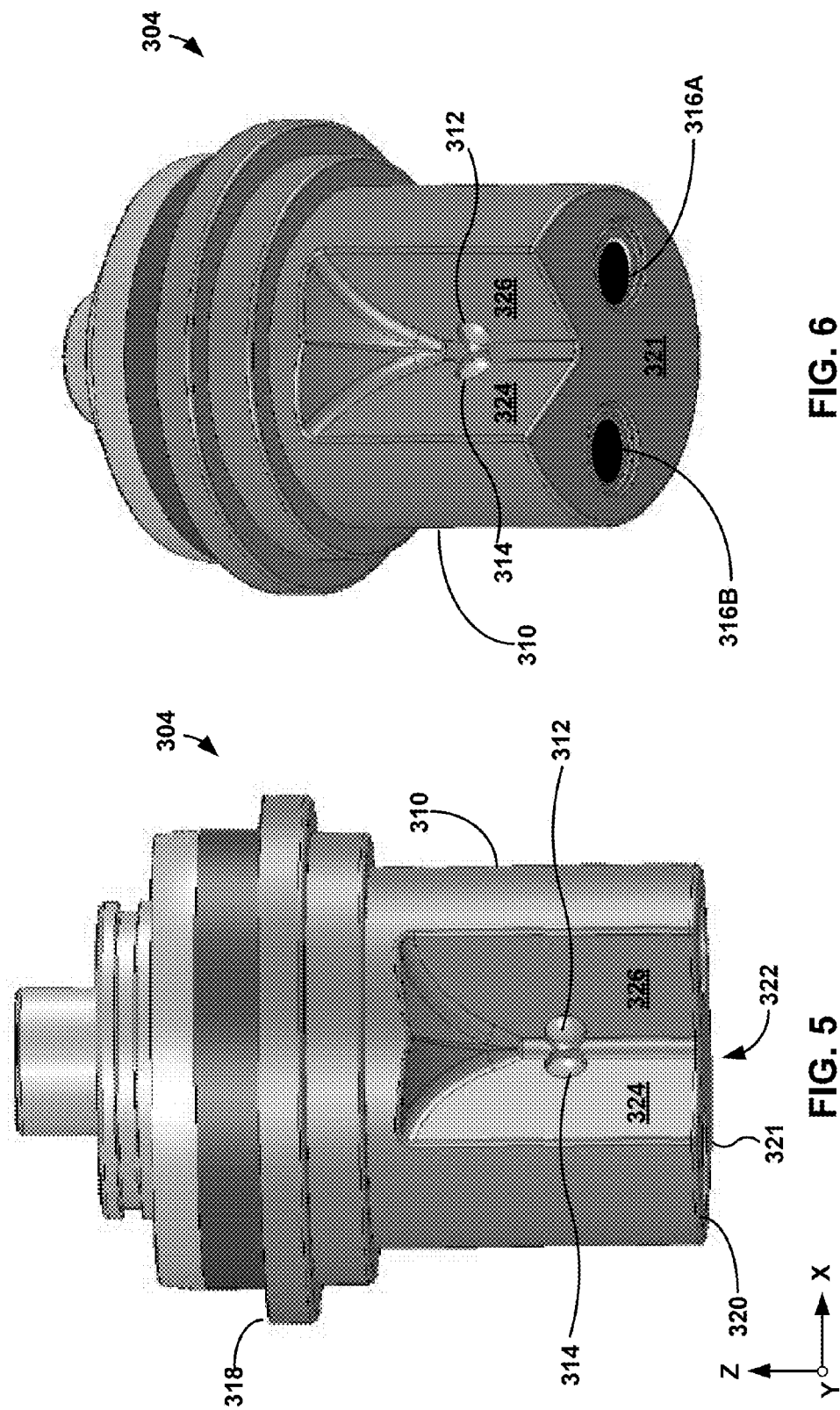
FIGS. 5 and 6 are alternative views of an example sensor head that may be used for the example optical sensor of FIGS. 3 and 4.

FIGS. 5 and 6 are alternative views of the example sensor head 304 illustrated in FIG. 3. As shown, sensor head 304 includes a sensor head housing 310, a first optical window 312, a second optical window 314, and at least one temperature sensor which, in the illustrated example, is shown as two temperature sensors 316A and 316B (collectively "temperature sensor 316"). Sensor head housing 310 defines a fluid impermeable structure that can house various components of sensor 300 such as, e.g., an optical emitter (FIG. 2) and an optical detector (FIG. 2). Sensor head housing 310 can be at least partially, and in some cases fully, immersed in a fluid. First optical window 312 defines an optically transparent section of sensor head housing 310 through which an optical emitter of sensor 300 can direct light into fluid within flow chamber 302, e.g., to cause fluorescent emissions. Second optical window 314 defines a different optically transparent section of sensor head housing 310 through which an optical detector of sensor 300 can receive fluorescent emissions emitted by the fluid within flow chamber 302. Temperature sensor 316 is configured to contact fluid within flow chamber 302 for determining a temperature of the fluid.

Sensor head housing 310 can define any suitable size and shape, and the size and shape of the sensor head housing can vary, e.g., depending on the number and arrangement of sensors carried by the housing. In the example of FIGS. 5 and 6, sensor head housing 310 defines an elongated body that extends from a proximal end 318 to a distal end 320 (i.e., in the Z-direction indicated on FIGS. 5 and 6) and includes a planar bottom surface 321. In some examples, sensor head housing 310 defines an elongated body that has a length in the Z-direction indicated on FIGS. 5 and 6 that is greater than a major width (e.g., in either X-direction or the Y-direction indicated on FIGS. 5 and 6). In other examples, sensor head housing 310 defines a length that is less than a major width of the housing.

While sensor head housing 310 is illustrated as defining a substantially circular cross-sectional shape (i.e., in the X-Y plane indicated on FIGS. 5 and 6), in other examples the housing can define other shapes. Sensor head housing 310 can define any polygonal (e.g., square, hexagonal) or arcuate (e.g., circular, elliptical) shape, or even combinations of polygonal and arcuate shapes. For instance, in some examples, sensor head housing 310 defines an angular cutout projecting towards an interior of the housing. The angular cutout may provide a location for positioning first optical window 312 and second optical window 314, e.g., to direct light from a light emitter through one window into a fluid sample and to receive fluorescent emissions generated by the fluid sample through another window. The angular cutout may also define a fluid channel for directing fluid between the first optical window and the second optical widow, e.g., when sensor head housing 310 is inserted into flow chamber 302 (FIG. 3) and fluid is flowing through the flow chamber.

In the example of sensor head housing 310, the housing includes an angular cutout 322 defined by a first planar surface 324 and a second planar surface 326. First planar surface 324 and second planar surface 326 each extend radially inwardly toward a center of sensor head housing 310. First planar surface 324 intersects second planar surface 326 to define an intersection angle between the two planar surfaces.

In some examples, the intersection angle between first planar surface 324 and second planar surface 326 is approximately 90 degrees, although the intersection angle can be greater than 90 degrees or less than 90 degrees and it should be appreciated that a sensor in accordance with the disclosure is not limited in this respect.

When sensor head housing 310 includes angular cutout 322, first optical window 312 can be positioned on one side of the angular cutout while second optical window 314 can be positioned on a different side of the angular cutout. Such an arrangement may reduce the amount of light that is emitted an optical emitter, transmitted through fluid within flow chamber 302, and detected by an optical detector, e.g., as compared to if first optical window 312 is positioned 180 degrees across from second optical window 314. Light generated by an optical emitter that is transmitted through a fluid and detected by an optical detector can potentially interfere with the ability of the optical detector to detect fluorescent emissions.

First optical window 312 and second optical window 314 are optically transparent portions of sensor head housing 310. First optical window 312 may be optically transparent to a frequency of light emitted by an optical emitter of sensor 300. Second optical window 314 may be optically transparent to a frequency of fluorescent emissions emitted by a fluid within fluid chamber. In operation, first optical window 312 and second optical window 314 may provide optical pathways for transmitting light generated by an optical emitter housed within sensor head housing 310 into a fluid in flow chamber 302 and for receiving fluorescent emissions emitted by the fluid by an optical detector housed within the sensor head housing.

In some examples, first optical window 312 and second optical window 314 are fabricated from the same material while in other examples, first optical window 312 is fabricated from a material that is different than the material used to fabricate second optical window 314. First optical window 312 and/or second optical window 314 may or may not include a lens, prism, or other optical device that transmit and refracts light. For example, first optical window 312 and/or second optical window 314 may be defined by a ball lens positioned within an optical channel extending through sensor head housing 310. The ball lens can be fabricated from glass, sapphire, or other suitable optically transparent materials.

In the examples of FIGS. 5 and 6, sensor head housing 310 includes a first optical window 312 for transmitting light into a fluid and a second optical window 314 for receiving fluorescent emissions from the fluid. First optical window 312 is positioned at substantially the same position along the length of sensor head housing 310 as second optical window 314 (i.e., in the Z-direction indicated on FIGS. 5 and 6). During use, fluid within flow chamber 302 (FIG. 3) may move between an optical axis extending through a center of first optical window 312 and an optical axis extending through a center of second optical window 314, e.g., by flowing in the positive Z-direction indicated on FIGS. 5 and 6. As the fluid moves past the optical windows, a light emitter may transmit light through first optical window 312 and into the fluid, causing molecules in the fluid to excite and fluoresce. Before the fluorescing fluid flows past second optical window 314, optical energy emitted by the fluorescing molecules may be received through second optical window 314 by an optical detector.

Although first optical window 312 is positioned at substantially the same position along the length of sensor head housing 310 as second optical window 314 in the example of sensor head 304, in other examples, first optical window 312 may be offset along the length of the sensor head housing from second optical window 314. For example, second optical window 314 may be positioned closer to proximal end 318 of sensor head housing 310 than first optical window 312. In addition, although sensor head 304 is illustrated as including a single optical window for emitting optical energy and a single optical window for receiving optical energy, in other examples, sensor head 304 can include fewer optical windows (e.g., a single optical window) or more optical windows (e.g., three, four, or more), and the disclosure is not limited in this respect.

During operation, sensor 300 can detect fluorescent emissions from a fluid flowing through flow chamber 302. The fluorescent emission data may be used to determine a concentration of a chemical species flowing through the flow chamber or to determine other properties of the fluid in the flow chamber. Depending on the application, additional data about the characteristics of the fluid flowing through flow chamber 302 beyond what can be obtained by fluorometric detection may be useful to monitor and/or adjust the properties of the fluid. For this reason, sensor 300 may include a different sensor (e.g., in addition to a fluorometric optical sensor) for sensing different properties of the fluid in flow chamber 302.

In the FIGS. 5 and 6, sensor head 304 includes temperature sensor 316 for measuring a temperature of fluid in flow chamber 302. Temperature sensor 316 can sense a temperature of the fluid and generate a signal corresponding to the sensed temperature. When configured with a temperature sensor, the temperature sensor can be implemented as a contact sensor that determines the temperature of a fluid by physically contacting the fluid or as a non-contact sensor that determines the temperature of the fluid without having the sensor physically contact the fluid. In other examples, sensor head 304 does not include temperature sensor 316.

In the example of sensor head 304, temperature sensor 316 is positioned on a different surface of sensor head housing 310 than optical windows 312, 314. Specifically, temperature sensor 316 is positioned on a bottom surface 321 of sensor head housing 310 while first optical windows 312 and second optical window 314 are positioned on a sidewall of the housing. In different examples, temperature sensor 316 may be flush with a surface (e.g., bottom surface 321) of sensor head housing 310, project outwardly from the surface of the sensor head housing, or be recessed relative to the surface of the sensor head housing.

Independent of the specific arrangement of temperature sensor 316 relative to sensor head housing 310, fluid within flow chamber 302 may flow adjacent the temperature sensor during operation of sensor 300. Fluid may flow adjacent temperature sensor 316 by flowing past and, optionally, in contact with, the temperature sensor so that the temperature sensor can sense a temperature of the fluid.

As briefly described above, sensor 300 (FIG. 3) includes flow chamber 302. Flow chamber 302 is configured to receive and contain sensor head 304. In particular, in the example of FIG. 3, flow chamber 302 is configured to receive sensor head 304 by moving the sensor head in the negative Z-direction shown on FIG. 3 until a surface of the sensor head abuts a surface of the fluid chamber. The abutting surface may be bottom surface 321 of sensor head housing 310 (FIGS. 5 and 6) or a different surface of the sensor head. Once suitably positioned within flow chamber 302, locking member 308 can be secured over flow chamber 302 and sensor head 304 to mechanical affix the sensor head to the flow chamber.

Figure 7:
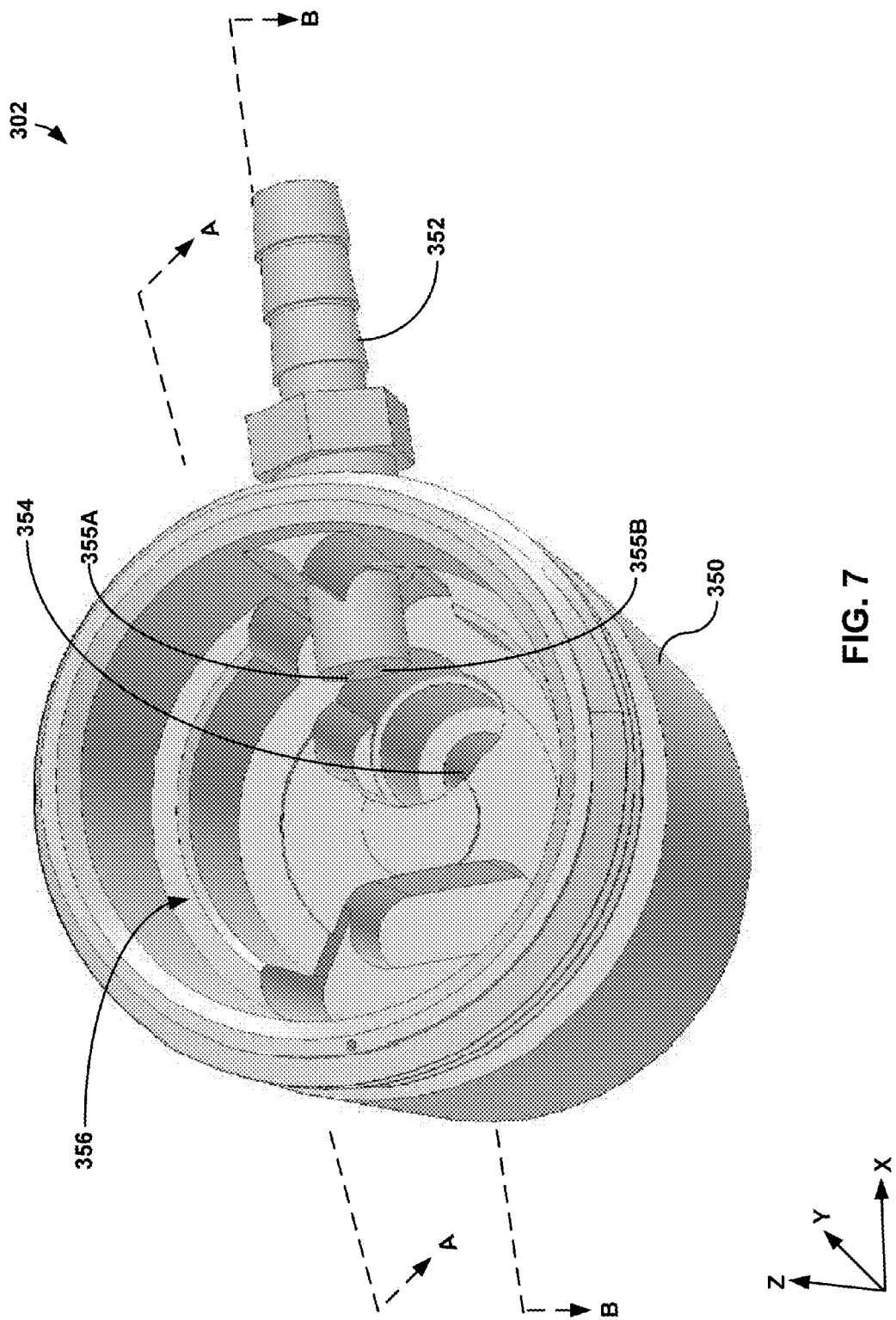
FIG. 7 is perspective top view of a flow chamber that may be used for the example optical sensor of FIGS. 3 and 4.
Figure 8:
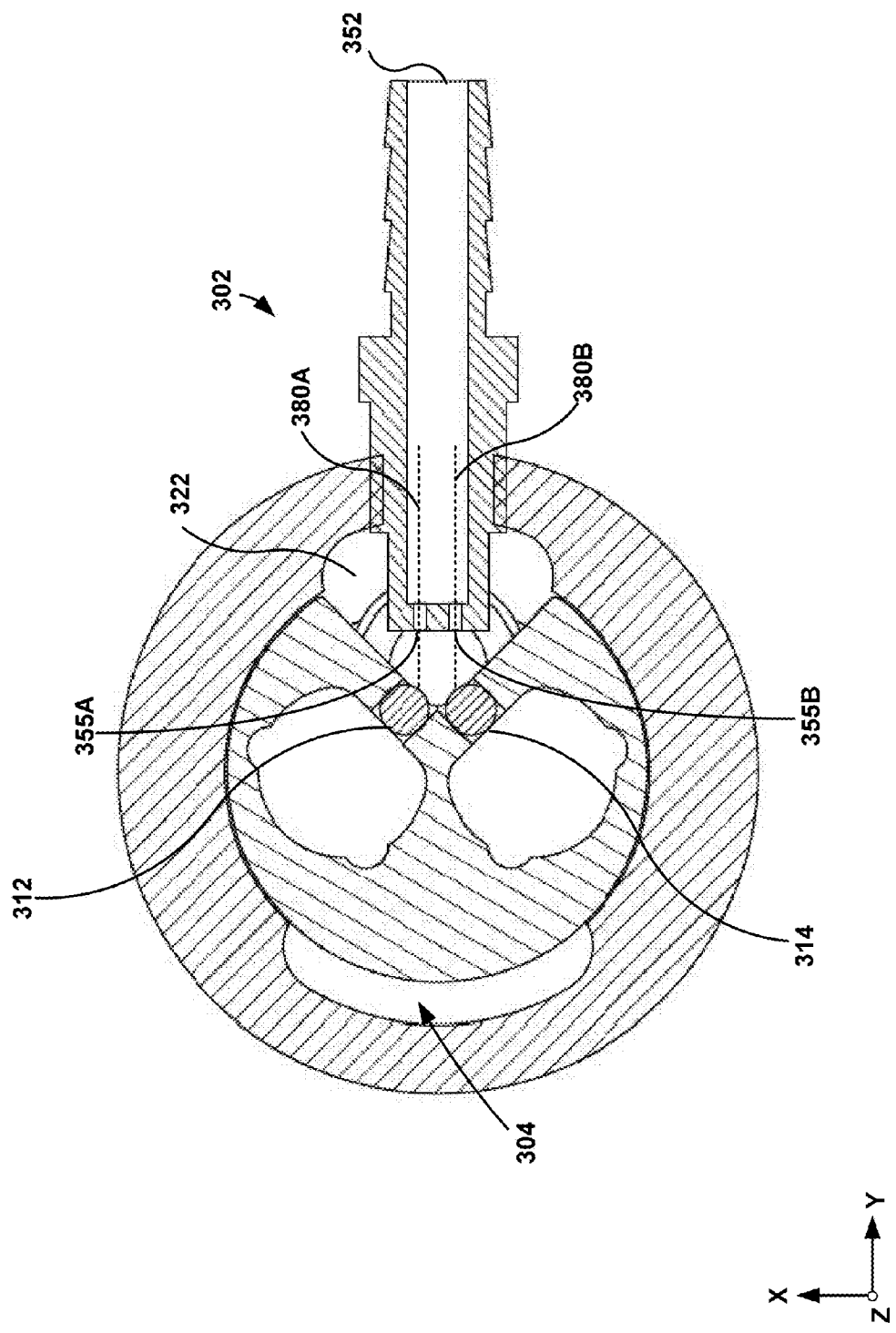
FIG. 8 is a cross-sectional top view of the example flow chamber of FIG. 7, shown with a sensor head inserted into the chamber, taken along the A-A cross-section line indicated on FIG. 7.
Figure 9:
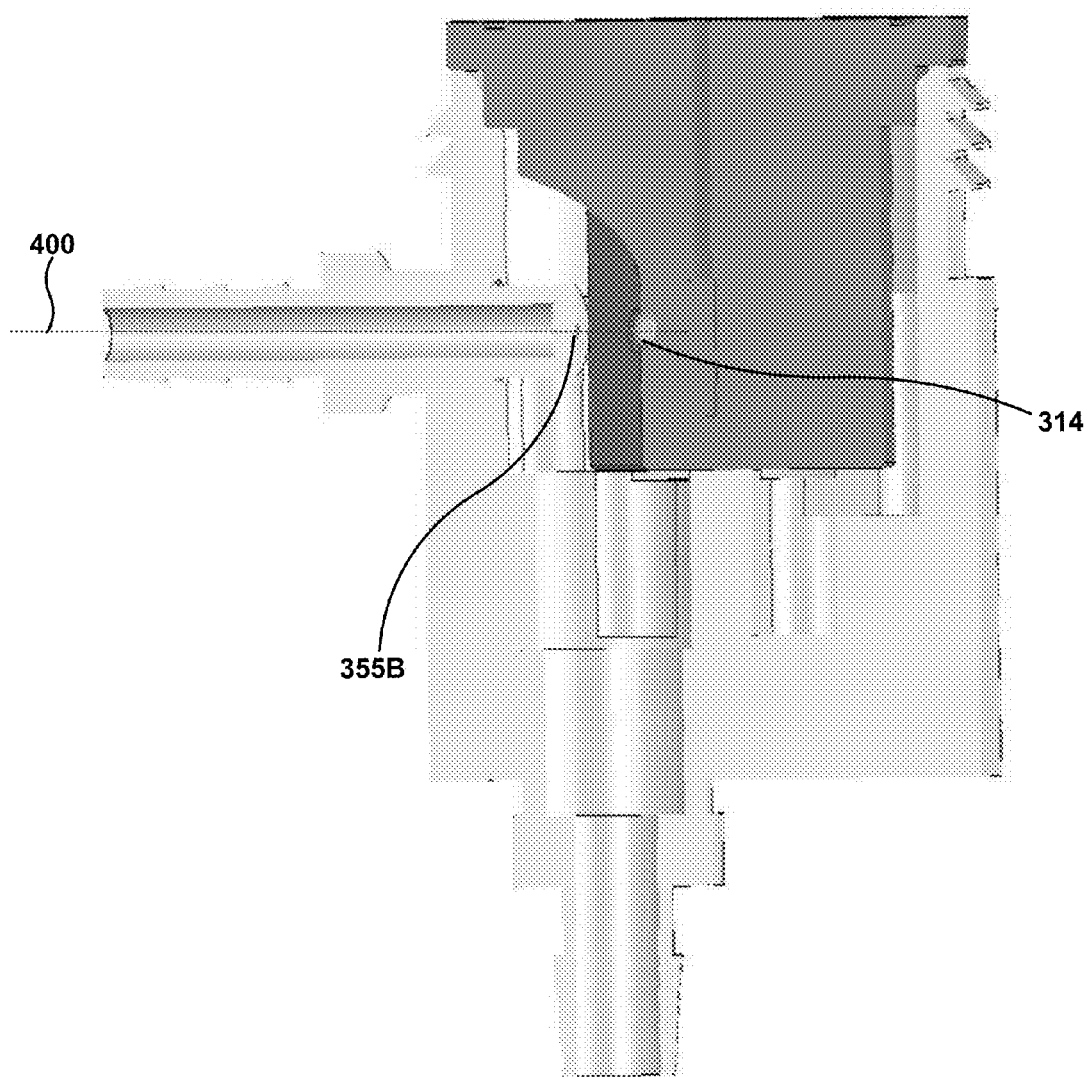
FIG. 9 is a cross-sectional side view of the example flow chamber of FIG. 7, shown with a sensor head inserted into the chamber, taken along the B-B cross-section line indicated on FIG. 7.

FIGS. 7-9 show different views of an example configuration of flow chamber 302. FIG. 7 is perspective top view of flow chamber 302 shown with sensor head 304 removed from the chamber. FIG. 8 is a cross-sectional top view of flow chamber 302 (with sensor head 304 inserted into the chamber) taken along the A-A cross-section line indicated on FIG. 7. FIG. 9 is a cross-sectional side view of flow chamber 302 (with sensor head 304 inserted into the chamber) taken along the B-B cross-section line indicated on FIG. 7.

In the illustrated example, flow chamber 302 includes a flow chamber housing 350, an inlet port 352, and an outlet port 354. Flow chamber housing 350 defines a cavity 356 that is configured (e.g., sized and shaped) to receive sensor head 304. Inlet port 352 extends through flow chamber housing 350 (e.g., a side wall of the housing) and is configured to convey fluid from outside of the housing to an interior of the housing. Outlet port 354 extends through flow chamber housing 350 (e.g., a side wall of the housing) and is configured to convey fluid from an interior of the housing to back outside of the housing. In operation, fluid may enter flow chamber 302 via inlet port 352, pass adjacent first optical window 312, second optical window 314, and temperature sensor 316 of sensor head 304, and discharge from the flow chamber via outlet port 354. When flow chamber 302 is used in online applications, fluid may flow through the chamber continuously for a period of time. For example, depending on the size and configuration of flow chamber 302, fluid may flow through the chamber at a rate ranging from 0.1 gallons per minute to 10 gallons per minute, although other flow rates are both possible and contemplated.

During operation of optical sensor 300, flow chamber 302 may receive fluid, e.g., from a downstream industrial process, that contain fouling materials (e.g., solid particles) and/or gas bubbles. These fouling materials and/or gas bubbles may accumulate within the flow chamber, inhibiting sensor head 304 from adequately detecting the characteristics of the fluid. In some examples according to the disclosure, inlet port 352 of flow chamber 302 defines at least one fluid nozzle that is configured to direct fluid entering flow chamber 302 against an optical window of sensor head 304. For example, in FIG. 8, inlet port 352 is illustrated as defining a first fluid nozzle 355A and a second fluid nozzle 355B (collectively "fluid nozzle 355"). When sensor head 304 (FIGS. 4 and 5) is inserted into flow chamber 302, first fluid nozzle 355A may direct fluid entering flow chamber 302 against first optical window 312 while second fluid nozzle 355B may direct fluid entering the flow chamber against second optical window 314. Fluid nozzle 355 of inlet port 352 may help reduce or eliminate the accumulation of fouling materials on sensor head 304, e.g., by causing incoming fluid to impact an optical window of the sensor head. The impacting fluid may prevent fouling materials from accumulating on the optical widow of sensor head 304 and/or dislodge accumulated fouling material from the optical window.

In addition, directing incoming fluid against an optical window of sensor head 304 may eliminate or reduce the formation of gas bubbles in the fluid, e.g., at least prior to being optically analyzed by the sensor head. In some applications, gas bubbles may form within a fluid moving through flow chamber 302 as the fluid contacts various surfaces of the flow chamber, e.g., causing dissolved gas to come out of solution and accumulate within the flow chamber. These gas bubbles may reduce the accuracy with which sensor head 304 of optical sensor 300 may determine a characteristic of the fluid. Directing fluid entering flow chamber 302 against an optical window of sensor head 304 may prevent gas bubbles from forming in the fluid and/or allow the fluid to be optically analyzed before gas bubbles form in the fluid.

Fluid nozzle 355 may be any structure that directs fluid entering flow chamber 302 against an optical window of sensor head 304. Fluid nozzle 355 may taper (e.g., in the negative Y-direction indicated on FIG. 8) to increase the speed of fluid flowing through the nozzle, expand to decrease the speed of fluid flowing through the nozzle, or maintain an equal cross-sectional area along the length of the nozzle. In the example of FIGS. 7-9, fluid nozzle 355 projects from an interior wall of flow chamber 302 into angular cutout 322 of sensor head 304. Fluid nozzle 355 defines a single fluid conduit that divides at a distal end into first fluid nozzle 355A and second fluid nozzle 355B. In other examples, first fluid nozzle 355A and second fluid nozzle 355B may each define a separate fluid pathway that projects from a wall of flow chamber 302. In addition, in still other examples, fluid nozzle 355 may not project from a wall of flow chamber 302. Rather, in these examples, fluid nozzle 355 may be flush with or recessed into a wall of flow chamber 302.

Fluid nozzle 355 defines at least one opening (e.g., two opening in the example of FIGS. 7-9) that projects fluid entering flow chamber 302 against an optical window of sensor head 304. The size of the fluid nozzle opening can vary, e.g., depending on the size of flow chamber 302 and the amount of fluid intended to be conveyed through the flow chamber. In addition, the size of the fluid nozzle opening may vary depending on the size of the optical window of sensor head 304. In some examples, fluid nozzle 355 defines an opening that has a cross-sectional area less than or equal to a cross-sectional area of an optical window of sensor head 304. For instance, in the example of FIGS. 7-9, first fluid nozzle 355A may define a cross-sectional area less than a cross-sectional area of first optical window 312 and/or second fluid nozzle 355B may define a cross-sectional area less than a cross-sectional area of second optical window 314. The cross-sectional area of first fluid nozzle 355A may be the same as or different than the cross-sectional area of second fluid nozzle 355B. Sizing first fluid nozzle 355A and second fluid nozzle 355B so the fluid nozzles have cross-sectional areas less than or equal to the cross-sectional areas of first optical window 312 and second optical window 314 may focus fluid entering flow chamber 302 on the optical windows. Rather than directing a comparatively larger fluid stream against first optical window 312 and/or second optical window 314, focusing the fluid stream into a comparatively smaller stream may increase the pressure and/or velocity of the fluid stream. This may increase the force with which the fluid stream impacts an optical window of sensor head 304 for removing fouling materials.

Fluid nozzle 355 can be positioned at a variety of different locations along flow chamber 302 and the position can vary, e.g., based on the location of the optical window of sensor head 304. In some examples, sensor head 304 includes a first optical and a second optical window that are a positioned within a common plane along sensor head housing 310. The common plane may be a common vertical plane (e.g., the Y-Z plane indicated on FIGS. 5 and 6) or a common horizontal plane (e.g., the X-Y plane indicated on FIGS. 5 and 6). For instance, in the example of sensor head 304 (FIGS. 5 and 6), first optical window 312 and second optical window 314 are positioned with a common horizontal plane passing through a center of each optical window. In some examples, fluid nozzle 355 may be positioned within the same plane as the optical window of sensor head 304 (e.g., the same plane as both first optical window 312 and second optical window 314). Such a location may minimize the distance fluid needs to travel from an end of the fluid nozzle to the optical window of the sensor head.

FIG. 9 is a cross-sectional side view of flow chamber 302 show with sensor head 304 inserted into the chamber. In this configuration, second fluid nozzle 355B is positioned within a common or same plane 400 with second optical window 314. Although not illustrated in the cross-sectional view, first fluid nozzle 355A may also be positioned within the common plane 400 with first optical window 312. When fluid nozzle 355 is positioned within a common plane 400 with an optical window of sensor head 304, fluid may travel within the plane (e.g., linearly) between the end of the fluid nozzle and the optical window during operation. Depending on the location of the fluid nozzle relative to the optical window, positioning fluid nozzle 355 within a common plane of an optical window of sensor head 304 may minimize the distance the fluid travels between the fluid nozzle and the optical window during operation. In turn, this may increase the force with the fluid impacts the optical window. That being said, in other examples, fluid nozzle 355 is not positioned within a common plane 400 with first optical window 312 and/or second optical window 314, and the disclosure is not limited in this respect.

Fluid nozzle 355 and, in particular, a fluid opening of fluid nozzle 355 can have a variety of different orientations relative to an optical window of sensor head 304. In general, orienting an opening of fluid nozzle 355 so that the opening is pointed towards the optical window of sensor head 304 may be useful for directing fluid against the optical window. During operation when fluid nozzle 355 has such a configuration, fluid discharging from the fluid nozzle may travel from the fluid nozzle to the optical window of sensor head 304 without contacting a wall surface or other internal surface of flow chamber 110. Instead, fluid exiting fluid nozzle 355 may directly contact the optical window of sensor head 304 prior to contact any other surface inside of flow chamber 302.

With further reference to FIG. 8, first fluid nozzle 355A defines a first fluid axis 380A extending through a center of the first fluid nozzle and second fluid nozzle 355B defines a second fluid axis 380B extending through a center of the second fluid nozzle. First fluid axis 380A extends through and intersects approximately a center of first optical window 312 such that, when fluid is flowing through first fluid nozzle 355A, a fluid stream exiting the nozzle is substantially centered on the optical window. Second fluid axis 380B extends through and intersects approximately a center of second optical window 314 such that, when fluid is flowing through second fluid nozzle 355B, a fluid stream exiting the nozzle is substantially centered on the optical window. In other examples, first fluid axis 380A and/or second fluid axis 380B may extend through a different portion of first optical window 312 and/or second optical window 314 other than a center of the optical windows or may not extend through the optical windows at all. For example, first fluid axis 380A and second fluid axis 380B may extend through wall of sensor head housing 310 such that, when fluid is flowing through first fluid nozzle 355A and second fluid nozzle 355B, fluid streams exiting the nozzles impact the wall of sensor head housing, e.g., before flowing against first optical window 312 and second optical window 314. Such a configuration may dissipate the force of an incoming fluid stream before contacting an optical window of sensor head 304.

During operation of flow chamber 302 in the example of FIGS. 7-9, fluid enters inlet port 352 of the flow chamber and travels through the inlet port and, in some examples through a portion of fluid nozzle 355, before splitting into first fluid nozzle 355A and second fluid nozzle 355B. A portion of the fluid entering the inlet port discharges through first fluid nozzle 355A while a different portion of the fluid entering the inlet port discharges through second fluid nozzle 355B. In some examples, all the fluid entering inlet port 352 discharges from the inlet port via first fluid nozzle 355A and second fluid nozzle 355B. For example, when fluid nozzle 355A defines an opening that is approximately the same size as an opening defined by second fluid nozzle 355B, approximately one half of the fluid entering inlet port 352 may discharge from the inlet port via first fluid nozzle 355A while the other half discharges from second fluid nozzle 355B. Upon discharging from fluid nozzle 355, fluid may travel from the distal tip of the fluid nozzle through a gaseous or liquid-filled space before contacting first optical window 312 and second optical window 314.

During operation of sensor head 304, the sensor head may emit light through first optical window 312 into a fluid flowing through flow chamber 302 and receive optical energy (e.g., fluorescent emissions) from the fluid through second optical window 314 for detecting a characteristic of the fluid. If fluid nozzle 355 projects from a wall of flow chamber 302 into optical pathways extending through the first optical window 312 and second optical window 314, the fluid nozzle may potentially cause optical interference with the sensor. Accordingly, in some examples when fluid nozzle 355 projects from a wall of flow chamber 302, the fluid nozzle is sized so as to help minimize or avoid optical interference by the nozzle.

FIG. 10 is another cross-sectional top view of flow chamber 302 (shown with sensor head 304 inserted into the chamber and without fluid nozzle 355 for purposes of illustration) taken along the A-A cross-section line indicated on FIG. 7. FIG. 10 illustrates example optical regions that may be defined by optical sensor 300. In this example, first optical window 312 is configured to project light from a light source into a first optical region 402 of angular cutout 322, and second optical window 314 is configured to receive light from second optical region 404 of the angular cutout. First optical region 402 overlaps with second optical region 404 adjacent optical first optical window 312 and second optical window 314. Depending on the orientation and design of sensor head 304, first optical region 402 may diverge from second optical region 404 as the optical regions extend away from first optical window 312 and second optical window 314, defining a third optical region 406. A fluid nozzle (not illustrated on FIG. 10) may be sized so that the nozzle projects into third optical region 406 without projecting into first optical region 402 and/or second optical region 404. Such sizing may help minimize the extent to which a projecting fluid nozzle causes optical interference with sensor head 304.

Optical sensor 300 in the example of FIGS. 7-10 includes two optical windows (optical window 312 and second optical window 314). For this reason, flow chamber 302 in this example is generally described as having two fluid nozzles, first fluid nozzle 355A and second fluid nozzle 355B. In other examples, flow chamber 302 may have fewer fluid nozzles (e.g., a single fluid nozzle) or more fluid nozzles (e.g., three, four, or more fluid nozzles), and the disclosure is not limited in this respect. For example, when sensor head 304 of optical sensor 300 has more than two optical windows, flow chamber 302 may have more than two fluid nozzles. In some examples, flow chamber 302 includes at least one fluid nozzle associated with each optical window of sensor head 304. Further, while first fluid nozzle 355A and second fluid nozzle 355B are illustrated in FIGS. 7-10 as being in fluid communication with a common inlet port, in other examples, each fluid nozzle may be defined by a separate inlet port extending through a side wall of flow chamber housing 350. Rather than partitioning incoming fluid inside of inlet port 352 of flow chamber 302, fluid entering the flow chamber may split or provided from different sources outside of the chamber and introduced into the flow chamber via different inlet ports.

As briefly discussed above with respect to FIG. 7, flow chamber 302 includes an inlet port 352 and an outlet port 354. Inlet port 352 is configured to connect to a conduit for conveying fluid from a source to an interior of flow chamber 302. Outlet port 354 is configured to connect to a conduit for conveying fluid away from flow chamber 302. Inlet port 352 and outlet port 354 can be positioned at any suitable location about the perimeter of flow chamber housing 350. In the example of FIGS. 7-10, inlet port 352 is positioned on a sidewall of the housing while outlet port 354 is positioned on a bottom surface of the housing. Inlet port 352 may be arranged at other locations relative to outlet port 354 and the disclosure is not limited in this respect.

With further reference to FIG. 3, sensor 300 also includes sensor cap 306 and locking member 308. Sensor cap 306 may define a cap that houses various electrical components of sensor 300. For example, sensor cap 306 may house at least a portion of an optical emitter (e.g., optical emitter 222) and/or an optical detector (e.g., optical detector 224) and/or a controller (e.g., controller 220) of sensor 300. Sensor cap 306 may be permanently affixed to (e.g., integrally molded with) sensor 300 or may be removable from sensor 300.

In some examples, sensor 300 does not include a controller and/or other electronic components that are physical housed with the sensor (e.g., in sensor cap 306). Rather, various components of sensor 300 may be located in one or more housings that are physically separate from the sensor and communicatively coupled to the sensor (e.g., via a wired or wireless connection). In one example, sensor cap 306 of sensor 300 is removable and sensor head 304 of the sensor is configured to connect to a handheld controller module. Example handheld controller modules that may be used with sensor 300 are described in US Patent Publication No. 2011/0240887, filed Mar. 31, 2010, and US Patent Publication No. 2011/0242539, also filed Mar. 31, 2010. The entire contents of these patent publications are incorporated herein by reference.

During operation, pressurized fluid may flow through flow chamber 302 of sensor 300. When sensor head 304 is designed to be removable from flow chamber 302, the pressurized fluid flowing through the flow chamber may try to force the sensor head out of the fluid chamber. For this reason, sensor 300 may include a locking member to lock sensor head 304 into flow chamber 302.

In the example of FIG. 3, sensor 300 includes locking member 308. Locking member 308 may help prevent sensor head 304 from disengaging with flow chamber 302 when pressurized fluid is flowing through the flow chamber. In some examples, locking member 308 is configured to secure sensor head 304 to flow chamber 302 by screwing the locking member over a portion of both the sensor head and the flow chamber. In different examples, locking member 308 may be configured to secure to sensor head 304 to flow chamber 302 using a different type of attachment feature such as, e.g., clips, bolts, or the like. By mechanically affixing sensor head 304 to flow chamber 302, sensor 300 may define fluid-tight cavity (e.g., except for inlet port 352 and outlet port 354) for receiving and analyzing a fluid sample.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a non-transitory computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. An optical sensor comprising:
   a sensor head that includes a first optical window, a second optical window, at least one light source, and at least one detector, wherein the at least one light source is configured to emit light through the first optical window into a flow of fluid within a first optical region and the at least one detector is configured to detect fluorescent emissions through the second optical window from the flow of fluid within a second optical region;
   a flow chamber that includes a housing defining a cavity into which the sensor head is inserted, an inlet port configured to communicate the flow of fluid from outside of the cavity to an interior of the cavity, and an outlet port configured to communicate the flow of fluid from the interior of the cavity to back outside of the cavity,
   wherein the inlet port defines a first fluid nozzle and a second fluid nozzle that each project into a third optical region located between the first optical region and the second optical region, the first fluid nozzle is configured to direct a portion of the flow of fluid against the first optical window, and the second fluid nozzle is configured to direct a portion of the flow of fluid against the second optical window.

2. The optical sensor of claim 1, wherein the first optical window and the second optical window are positioned within a same plane, and the first fluid nozzle and the second fluid nozzle are positioned within the same plane as the first optical window and the second optical window.

3. The optical system of claim 1, wherein the first fluid nozzle defines a first fluid axis extending through a center of the first fluid nozzle, the second fluid nozzle defines a second fluid axis extending through a center of the second fluid nozzle, and the first fluid axis intersects approximately a center of the first optical window and the second fluid axis intersects approximately a center of the second optical window.

4. The optical sensor of claim 1, wherein the sensor head includes a sensor housing extending from a proximal end to a distal end, the sensor housing including an angular cutout defined by a first planar surface that intersects a second planar surface, wherein the first optical window is positioned in the first planar surface and the second optical window is positioned on the second planar surface.

5. The optical sensor of claim 4, wherein the first planar surface intersects the second planar surface to define an approximately 90 degree angle, the first optical window and the second optical window are positioned within a same plane between the proximal end and the distal end of the sensor housing, and the first fluid nozzle and the second fluid nozzle are positioned within the same plane as the first optical window and the second optical window.

6. The optical sensor of claim 4, wherein the first fluid nozzle and the second fluid nozzle project away from a wall of the flow chamber into the angular cutout.

7. The optical sensor of claim 1, wherein the first optical window and the second optical window each comprise a ball lens.

8. The optical sensor of claim 1, wherein the inlet port provides a single fluid nozzle projecting into the third optical region and splits at a terminal end into the first fluid nozzle and the second fluid nozzle.

9. The optical sensor of claim 1, wherein an opening defined by the first fluid nozzle is approximately a same size as an opening defined by the second fluid nozzle.

10. A method comprising:
directing fluid through a first fluid nozzle of a flow chamber against a first optical window of a sensor head; and
directing fluid through a second fluid nozzle of the flow chamber against a second optical window of the sensor head,
wherein the sensor head includes at least one light source configured to emit light through the first optical window into a flow of fluid within a first optical region and at least one detector configured to receive optical energy through the second optical window from the flow of fluid within a second optical region, and
wherein the first fluid nozzle and the second fluid nozzle each project into a third optical region located between the first optical region and the second optical region.

11. The method of claim 10, wherein the first optical window and the second optical window are positioned within a same plane, and directing fluid through the first fluid nozzle comprises directing fluid within the same plane as the first optical window, and directing fluid through the second fluid nozzle comprises directing fluid within the same plane as the second optical window.

12. The method of claim 10, wherein the first fluid nozzle defines a first fluid axis extending through a center of the first fluid nozzle, the second fluid nozzle defines a second fluid axis extending through a center of the second fluid nozzle, and directing fluid through the first fluid nozzle comprises directing fluid so the first fluid axis intersects approximately a center of the first optical window, and directing fluid through the second fluid nozzle comprises directing fluid so the second fluid axis intersects approximately a center of the second optical window.

13. The method of claim 10, wherein the sensor head includes a sensor housing extending from a proximal end to a distal end, the sensor housing including an angular cutout defined by a first planar surface that intersects a second planar surface, wherein the first optical window is positioned in the first planar surface and the second optical window is positioned on the second planar surface.

14. The method of claim 13, wherein the first fluid nozzle and the second fluid nozzle project away from a wall of the flow chamber into the angular cutout.

* * * * *